US008669351B2

(12) United States Patent
Matalon et al.

(10) Patent No.: US 8,669,351 B2
(45) Date of Patent: Mar. 11, 2014

(54) ANTIBODIES TO POLYPEPTIDES ENCODED BY ASPARTOACYLASE POLYNUCLEOTIDES

(75) Inventors: Reuben Matalon, Coral Gables, FL (US); Rajinder Kaul, Miami, FL (US); Guang Ping Cao, Miami, FL (US); Kuppareddi Balamurugan, Miami, FL (US); Kimberlee Michals-Matalon, Coral Gables, FL (US)

(73) Assignee: Miami Children's Hospital, Miami, FL (US)

( * ) Notice: Subject to any disclaimer, the term of this patent is extended or adjusted under 35 U.S.C. 154(b) by 1097 days.

(21) Appl. No.: 11/541,665

(22) Filed: Oct. 3, 2006

(65) Prior Publication Data

US 2007/0026452 A1    Feb. 1, 2007

Related U.S. Application Data

(63) Continuation of application No. 09/965,807, filed on Oct. 1, 2001, now Pat. No. 7,217,547, which is a continuation of application No. 08/128,020, filed on Sep. 29, 1993, now abandoned.

(51) Int. Cl.
*C07K 16/40* (2006.01)
*C12P 21/08* (2006.01)
*C12N 5/12* (2006.01)
*C12N 5/16* (2006.01)

(52) U.S. Cl.
USPC ............... 530/388.26; 530/388.1; 530/387.9; 435/326; 435/346

(58) Field of Classification Search
None
See application file for complete search history.

(56) References Cited

U.S. PATENT DOCUMENTS 4,931,385 A * 6/1990 Block et al. .................. 435/7.94

OTHER PUBLICATIONS

Falkenberg et al. J. Clin. Chem. Clin Biochem. 1984, 22:867-82.*
Metzroth et al. Infect. Immun. 1993, 61:2445-2452.*
Bost et al. Immunological Investigation, 1988, 17:577-586.*
Bendayan The Journal of Histochemistry and Cytochemistry 1995 43:881-886.*
Attwood Science 290: 471-473, 2000.*
Skolnick et al. Trends in Biotech. 18: 34-39, 2000.*
Lederman et al. Molecular Immunology 28: 1171-1181, 1991.*
Li et al. PNAS 77: 3211-3214, 1980.*
Houghten et al. New Approaches to Immunization, Vaccines86, Cold Spring Harbor Laboratory, p. 21-25, 1986.*
R. Matalon et al., Aspartoacylase Deficiency: The Enzyme Defect in Canavan Disease; Journal of Inherited Metabolic. Disease 12 Suppl. 2 (1989); pp. 329-331.
Leong et al., *Methods in Enzymology*, 78: 87-101 (1981).
Hagenfeldt et al., J. Inherit.Metab. Dis. 10 (2) 135-141 (1987).
D'Adamo et al., J. Neurochem. 28 (4) 739-44 (1977).
Kaul et at., J. Neurochem. 56 (1) 129-135 (1991).
Matalon et at., Am. J. Med. Genet. 29: 463-471 (1988).
Adamo et al., J. Neurochem. 28 (4) 739-44 (1977).
Methods in Enzymology: Table of Contents, vol. 187, pp. 1-894.
Guide to Protein Purification. 1990. Edited by M.P. Deutscher.
Komberh, A. Why Purify Enzymes? pp. 1-5. Methods in Enzymology, 1990, vol. 192, Chapter 1, pp. 1-5.
Kaul et al. (a), Aspartoacyclase Deficiency in Canavan Disease: Partial Purification and Distribution in Mammalian Brain, 1988, American Journal of Human Genetics, vol. 43, p. A10.
Kaul et al. (c), Cloning of the Human Aspartoacyclase cDNA and a Common Missense Mutation in Canavan Disease, Oct. 1993, vol. 5, pp. 118-123.

* cited by examiner

*Primary Examiner* — Daniel E Kolker
(74) *Attorney, Agent, or Firm* — Millen, White, Zelano & Branigan, P.C.

(57)    ABSTRACT

Canavan disease, an autosomal recessive leukodystrophy, is caused by deficiency of aspartoacylase and accumulation of N-acetylaspartic acid in brain. Human aspartoacylase (ASP) cDNA spanning 1,435 bp has been cloned and expressed in *E. coli*. A base change, a854>c, has been found in 85% of the 34 Canavan alleles tested so far, which results in a missense glu285>ala mutation that is predicted to be part of the catalytic domain of aspartoacylase. The invention therefore provides nucleic acid sequences, genes, polypeptides, antibodies, vectors containing the gene, host cells transformed with vectors containing the gene, animal models for the disease, methods for expressing the polypeptide, genetic screening methods and kits, diagnostic methods and kits, methods of treating Canavan disease and methods of genetic therapy for the disease.

17 Claims, 14 Drawing Sheets

```
     TTGTAACAGA AAATTAAAAT ATACTCCACT CAAGGGAATT CTGTACTTTG CCCTTTTGGT  -99
     AAGTCTCAT TTACATTTCT AAACCTTTCT TAAGAAAATC GAATTTCCTT TGATCTCTCT   -39
  1  TCTGAATTGC AGAAATCAGA TAAAAACTAC TTGGTGAA ATG ACT TCT TGT CAC ATT   18
                                              -1  M   T   S   C   H   I

7  GCT GAA GAA CAT ATA CAA AAG GTT GCT ATC TTT GGA GGA ACC CAT GGG     66
      A   E   E   H   I   Q   K   V   A   I   F   G   G   T   H   G

23  AAT GAG CTA ACC GGA GTA TTT CTG GTT AAG CAT TGG CTA GAG AAT GGC    114
      N   E   L   T   G   V   F   L   V   K   H   W   L   E   N   G

39  GCT GAG ATT CAG AGA ACA GGG CTG GAG GTA AAA CCA TTT ATT ACT AAC    162
      A   E   I   Q   R   T   G   L   E   V   K   P   F   I   T   N

55  CCC AGA GCA GTG AAG AAG TGT ACC AGA TAT ATT GAC TGT GAC CTG AAT    210
      P   R   A   V   K   K   C   T   R   Y   I   D   C   D   L   N

71  CGC ATT TTT GAC CTT GAA AAT CTT GGC GAA ATA ATG AAA GAT TTG        258
      R   I   F   D   L   E   N   L   G   E   I   M   K   D   L

87  CCA TAT GAA GTG AGA AGG GCT CAA GAA ATA ATT CAT TTA TTT GGT CCA    306
      P   Y   E   V   R   R   A   Q   E   I   I   H   L   F   G   P

103  AAA GAC AGT GAA GAT TCC TAT GAC ATT CTT ATT CTT GAG GAT TCC AGG    354
      K   D   S   E   D   S   Y   D   I   L   I   L   E   D   S   R

119  ACC TCT AAC ATG GGG TGC ACT TAC ATT CAT TAC ATT AAG ACT CTG GCT    402
      T   S   N   M   G   C   T   Y   I   H   Y   I   K   T   L   A

135  TTT TTA ATT CAG ATG TTT CAT TAC ATT GAG CAT CCT TCC CTC AAA TAT    450
      F   L   I   Q   M   F   H   Y   I   E   H   P   S   L   K   Y

151  CCC TGC TAC GTT TAT CTG ATT GAG CAT CCT TCC CTC AAA TAT GCG ACC    498
      P   C   Y   V   Y   L   I   E   H   P   S   L   K   Y   A   T

```
     ACT CGT TCC ATA GCC AAG TAT CCT GTG GGT ATA GAA GTT GGT CCT CAG  546
183   T   R   S   I   A   K   Y   P   V   G   I   E   V   G   P   Q
     CCT CAA GGG GTT CTG AGA GCT CTG GAT ATC TTG GAT CAA ATG AGA AAA ATG  594
199   P   Q   G   V   L   R   A   L   D   I   L   D   Q   M   R   K   M
     ATT AAA CAT GCT CTT TTT ATA CAT CAT TTC AAT GAA GGA AAA GAA  642
215   I   K   H   A   L   F   I   H   H   F   N   E   G   K   E
     TTT CCT CCC TGC GCC ATT GAG GTC TAT AAA ATT ATA GAG AAA GTT GAT  690
231   F   P   P   C   A   I   E   V   Y   K   I   I   E   K   V   D
     TAC CCC CGG GAT GAA AAT GGA GAA ATT GCT CAT CCT ATC ATC CAT CCT AAT  738
247   Y   P   R   D   E   N   G   E   I   A   H   P   I   I   H   P   N
     CTG CAG GAT CAA GAC TGG AAA CCA CTG CAT CCT GGG GAT CCC ATG TTT  786
263   L   Q   D   Q   D   W   K   P   L   H   P   G   D   P   M   F
     TTA ACT CTT GAT GGG AAG ACG ATC CCA CTG GGC GGA GAC TGT ACC GTG  834
279   L   T   L   D   G   K   T   I   P   L   G   G   D   C   T   V
     TAC CCC GTG TTT GTG AAT GAG GCC GCA TAT TAC AAA GAA AAG GAA GCT  882
295   Y   P   V   F   V   N   E   A   A   Y   Y   K   E   K   E   A
     TTT GCA AAG ACA ACT AAA ACG CTC AAT GCA AAA AGT ATT CGC TGC  930
311   F   A   K   T   T   K   T   L   N   A   K   S   I   R   C
     TGT TTA CAT TAG AA ATCACTTCCA GCTTACATCT TACACGGTGT CTTACAAATT  984
     CTGCTAGTCT GTAAGCTCCT TAAGAGTAGG GTTGTGCCTT ATTCAACTGC ATACATAGCT 1044
     CCTAGCACAG TGCCTTATTC GGTAGGCATC TAAGCAAATT TCTTAAATTA ATTAATATAT 1104
     CTTTAAAGAT ATCATATTTT ATGTATGTAG CTTATTCAAA GAAGTGTTTC CTATTTCTAT 1164
     ATAGTTTATT ATACATGATA CTTGGGTAGC TCAACATTCT TAATAAACAG CCTTTGTATT 1224
     CAGAAATATAAAATTGAAATA GATATATATA AAGTAAAAA AAAAAAAAAA AAA          1277
```

FIG.1B

```
          10v        20v        30v        40v        50v
HLASP     MTSCHIAEEHIQKVAIFGGTHGNELTGVFLVKHWLENGAEIQRTGLEVKPF
          MTSCH:AE:.I:KVAIFGGTHGNELTGVFLVKHWLEN::EIQRTGLEVKPF
BASPCDNA  MTSCHVAEDPIKKVAIFGGTHGNELTGVFLVKHWLENSTEIQRTGLEVKPF
          10^       20^        30^        40^        50^
          60v        70v        80v        90v       100v
HLASP     ITNPRAVKKCTRYIDCDLNRIFDLENLGKKMSEDLPYEVRRAQEINHLFGP
          ITNPRAVKKCTRYIDCDLNR:FD ENLGKK.SEDLPYEVRRAQEINHLFGP
BASPCDNA  ITNPRAVKKCTRYIDCDLNRVFDPENLGKKKSEDLPYEVRRAQEINHLFGP
          60^        70^       80^        90^       100^
         110v       120v       130v       140v       150v
HLASP     KDSEDSYDIIFDLHN'TTSNMGCTLILEDSRNNFLIQMFHYIKTSLAPLPCY
          KDSEDSYDIIFDLHN'TTSNMGCTLILEDSRN:FLIQMFHYIKTSLAPLPCY
BASPCDNA  KDSEDSYDIIFDLHN'TTSNMGCTLILEDSRNDFLIQMFHYIKTSLAPLPCY
         110^       120^       130^       140^       150^
         160v       170v       180v       190v       200v
HLASP     VYLIEHPSLKYATTRSIAKYPVGIEVGPQPQGVLRADILDQMRKMIKHALD
          VYLIEHPSLKYATTRSIAKYPVGIEVGPQPQGVLRADILDQMRKMI:HALD
BASPCDNA  VYLIEHPSLKYATTRSIAKYPVGIEVGPQPQGVLRADILDQMRKMIQHALD
         160^       170^       180^       190^       200^
         210v       220v       230v       240v       250v
HLASP     FIHHFNEGKEFPPCAIEVYKIIEKVDYPRDENGEIAAIIHPNLQDQDWKPL
          FIH:FNEGKEFPPCAIEVYKI: KVDYPR:E:GEI:AIIHP:LQDQDWKPL
BASPCDNA  FIHNFNEGKEFPPCAIEVYKIMRKVDYPRNESGEISAIIHPKLQDQDWKPL
         210^       220^       230^       240^       250^
         260v       270v       280v       290v       300v
HLASP     HPGDPMFLTLDGKTIPLGGDCTVYPVFVNEAAYYEKKEAFAKTTKLTLNAK
          HP.DP:FLTLDGKTIPLGGD TVYPVFVNEAAYYEKKEAFAKTTKLTLNA:
BASPCDNA  HPEDPVFLTLDGKTIPLGGDQTVYPVFVNEAAYYEKKEAFAKTTKLTLNAN
         260^       270^       280^       290^       300^
         310v
HLASP     SIRCCLH
          SIR..LH
BASPCDNA  SIRSSLH
         310^
```

FIG. 2

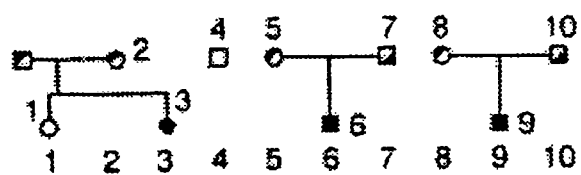
FIG. 6A
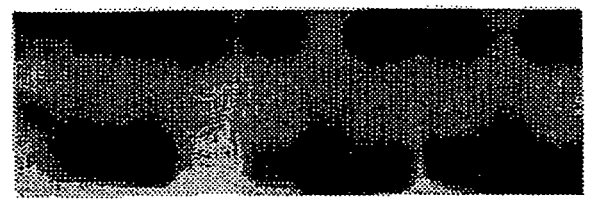
FIG. 6B

```
            E A M                              M      E M        N DSNDSBB
            A S A                              B      C N        L STCSESS
            M P E                              O      5 L        A AYOACAA
            1 E 3                              2      7 1        4 11111JJ
              /                                                  /////
ATGACTTCTTGTCACATTGCTGAAGAACATATACAAAAGGTTGCTATCTTTGGAGGAACC
----.----+----.----+----.----+----.----+----.----+----.----+   60
TACTGAAGAACAGTGTAACGACTTCTTGTATATGTTTTCCAACGATAGAAACCTCCTTGG m   t   s   c   h   i   a   e   e   h   i   q   k   v   a   i   f   g   g   t
 ↑
 └── START SITE

----.----+----.----+----.----+----.----+----.----+----.----+

✓
        N     A    B B H         T S M          R M       H   H H D    T H
        L     L    S C P         R P S          M A       I   H A D    F N
        A     U    A A A         U O E          A E       N   A E E    I F
        3     1    W 7 2         9 1 1          1 1       P   1 2 1    1 1
                   / /           ↓ /             /            /  /      /
CATGGGAATGAGCTAACCGGAGTATTTCTGGTTAAGCATTGGCTAGAGAATGGCGCTGAG
----.----+----.----+----.----+----.----+----.----+----.----+   120
GTACCCTTACTCGATTGGCCTCATAAAGACCAATTCGTAACCGATCTCTTACCGCGACTC h   g   n   e   l   t   g   v   f   l   v   k   h   w   l   e   n   g   a   e

----.----+----.----+----.----+----.----+----.----+----.----+

M                             B
              N                             P
              L                             M
              1                             1
ATTCAGAGAACAGGGCTGGAGGTAAAACCATTTATTACTAACCCCAGAGCAGTGAAGAAG
----.----+----.----+----.----+----.----+----.----+----.----+   180
TAAGTCTCTTGTCCCGACCTCCATTTTGGTAAATAATGATTGGGGTCTCGTCACTTCTTC i   q   r   t   g   l   e   v   k   p   f   i   t   n   p   r   a   v   k   k

```
CR    M            M        TH
SS    B            A        FN
PA    O            E        IF
61    2            3        11
                            /
TGTACCAGATATATTGACTGTGACCTGAATCGCATTTTTGACCTTGAAAATCTTGGCAAA
----.----+----.----+----.----+----.----+----.----+----.----+   240
ACATGGTCTATATAACTGACACTGGACTTAGCGTAAAAACTGGAACTTTTAGAACCGTTT c  t  r  y  i  d  c  d  l  n  r  i  f  d  l  e  n  l  g  k

----.----+----.----+----.----+----.----+----.----+----.----+

NM                      BN
            DB                      AS
            EO                      NP
            12                      22
             /
AAAATGTCAGAAGATTTGCCATATGAAGTGAGAAGGGCTCAAGAAATAAATCATTTATTT
----.----+----.----+----.----+----.----+----.----+----.----+   300
TTTTACAGTCTTCTAAACGGTATACTTCACTCTTCCCGAGTTCTTTATTTAGTAAATAAA k  m  s  e  d  l  p  y  e  v  r  r  a  q  e  i  n  h  l  f

----.----+----.----+----.----+----.----+----.----+----.----+

A           TH             M                             S
V           FN             B                             P
A           IF             O                             O
2           11             2                             1
             /
GGTCCAAAAGACAGTGAAGATTCCTATGACATTATTTTTGACCTTCACAACACCACCTCT
----.----+----.----+----.----+----.----+----.----+----.----+   360
CCAGGTTTTCTGTCACTTCTAAGGATACTGTAATAAAAACTGGAAGTGTTGTGGTGGAGA g  p  k  d  s  e  d  s  y  d  i  i  f  d  l  h  n  t  t  s

```
       MN  A    HBN  M           TH  E  AS           TM
       NL  P    GSS  N           FN  C  PC           RS
       LA  L    IIP  L           IF  R  YR           UE
       13  1    AH2  1           11  2  11           91
        /  /    / /  /            /  /  /             ↓
AACATGGGTGCACTCTTATTCTTGAGGATTCCAGGAATAACTTTTTAATTCAGATGTTT
----.----+----.----+----.----+----.----+----.----+----.----+  420
TTGTACCCCACGTGAGAATAAGAACTCCTAAGGTCCTTATTGAAAAATTAAGTCTACAAA n  m  g  c  t  l  i  l  e  d  s  r  n  n  f  l  i  q  m  f

----.----+----.----+----.----+----.----+----.----+----.----+

✓
      TM              N              M  F              E
      RS              L              A  O              C
      UE              A              E  K              O
      91              4              2  1              B
       ↓
CATTACATTAAGACTTCTCTGGCTCCACTACCCTGCTACGTTTATCTGATTGAGCATCCT
----.----+----.----+----.----+----.----+----.----+----.----+  480
GTAATGTAATTCTGAAGAGACCGAGGTGATGGGACGATGCAAATAGACTAACTCGTAGGA h  y  i  k  t  s  l  a  p  l  p  c  y  v  y  l  i  e  h  p

----.----+----.----+----.----+----.----+----.----+----.----+

S              M                                      A
  F              N                                      V
  A              L                                      A
  N              1                                      2

TCCCTCAAATATGCGACCACTCGTTCCATAGCCAAGTATCCTGTGGGTATAGAAGTTGGT
----.----+----.----+----.----+----.----+----.----+----.----+  540
AGGGAGTTTATACGCTGGTGAGCAAGGTATCGGTTCATAGGACACCCATATCTTCAACCA s  l  k  y  a  t  t  r  s  i  a  k  y  p  v  g  i  e  v  g

```
              S      PBMOD      F                  ESASBBSBXBNMDDB
              F      SIBPP      O                  CEPCSSFIHALBPPI
              C      TNONN      K                  RCYRAAANOMAONNN
              1      11121      1                  2111JJN12141211
                     ////                          ///  ////////
      GCTATCATCCATCCTAATCTGCAGGATCAAGACTGGAAACCACTGCATCCTGGGGATCCC
      ----.----+----.----+----.----+----.----+----.----+----.----+   780
      CGATAGTAGGTAGGATTAGACGTCCTAGTTCTGACCTTTGGTGACGTAGGACCCCTAGGG a   i   i   h   p   n   l   q   d   q   d   w   k   p   l   h   p   g   d   p

----.----+----.----+----.----+----.----+----.----+----.----+

N      TM         B      MDBBBDBMA  BBAB      CR         CR
              L      RS         B      BPBSPPIBL  SSCS      SS         SS
              A      UE         V      ONSCUNNOW  ILIM      PA         PA
              3      91         2      121911122  Y112      61         61
              /      //         /      / ////     ///
      ATGTTTTTAACTCTTGATGGAAGACGATCCCACTGGGCGGAGACTGTACCGTGTACCCC
      ----.----+----.----+----.----+----+----.----+----.----+   840
      TACAAAAATTGAGAACTACCCTTCTGCTAGGGTGACCGCCTCTGACATGGCACATGGGG m   f   l   t   l   d   g   k   t   i   p   l   g   g   d   c   v   y   p

----.----+----.----+----.----+----.----+----.----+----.----+

SM             HIFA                H    A
              PN             ATNC                I    L
              OL             EAUI                N    U
              11             31H1                3    1
              /      *       //                                    *
      GTGTTTGTGAATGAGGCCGCATATTACGAAAAGAAAGAAGCTTTTGCAAAGACAACTAAA
      ----.----+----.----+----.----+----.----+----.----+----.----+   900
      CACAAACACTTACTCCGGCGTATAATGCTTTTCTTTCTTCGAAAACGTTTCTGTTGATTT v   f   v   n   e   a   a   y   y   e   k   k   e   a   f   a   k   t   t   k
                                                                              ┌─────────┐
                                                                              │ a854>c  │
      ----.----+----.----+----.----+----.----+----.----+----.----+            │ E285>A  │
                                                                              └─────────┘
```

FIG. 7(e)

```
        S              B           HIF     E                              A
        P              B           NTN     C                              L
        O              V           FAU     1                              U
        1              1           31H     5                              1         ┌─────────┐
                       *                   /                                        │c914>a   │
     CTAACGCTCAATGCAAAAAGTATTCGCTGCTGTTTACATTAGAAATCACTTCCAGCTTAC│A305>E  │
     ----.----+----.----+----.----+----.----+----.----+----.----+    960  └─────────┘
     GATTGCGAGTTACGTTTTTCATAAGCGACGACAAATGTAATCTTTAGTGAAGGTCGAATG l  t   l   n   a   k   s   i   r   c   c   l   h   .   k   s   l   p   a   y

----.----+----.----+----.----+----.----+----.----+----.----+

/
                          RM              A       ATM
                          MA              L       FRS
                          AE              U       LUE
                          Il              1       291
                           /                       /
     ATCTTACACGGTGTCTTACAAATTCTGCTAGTCTGTAAGCTCCTTAAGAGTAGGGTTGTG
     ----.----+----.----+----.----+----.----+----.----+----.----+    1020
     TAGAATGTGCCACAGAATGTTTAAGACGATCAGACATTCGAGGAATTCTCATCCCAACAC i   l   h   g   v   l   q   i   l   l   v   c   k   l   l   k   s   r   v   v

----.----+----.----+----.----+----.----+----.----+----.----+

B   A     RM                K       D       S
                      S   L     MA                N       D       F
                      P   U     AE                F       E       A
                      W   1     Il                3       1       N
                                /
     CCTTATTCAACTGCATACATAGCTCCTAGCACAGTGCCTTATTCGGTAGGCATCTAAGCA
     ----.----+----.----+----.----+----.----+----.----+----.----+    1080
     GGAATAAGTTGACGTATGTATCGAGGATCGTGTCACGGAATAAGCCATCCGTAGATTCGT p   y   s   t   a   y   i   a   p   s   t   v   p   y   s   v   g   i   .   a

```
         ↓    ↓   ↓           ↓
         TM   ATM PATM        TDM      E                         A
         RS   SRS ASRS        RRS      C                         L
         UE   EUE CEUE        UAE      R                         U
         91   191 1191        911      V                         1
         /    //  ///         /
AATTTCTTAAATTAATTAATATATCTTTAAAGATATCATATTTTATGTATGTAGCTTATT
----.----+----.----+----.----+----.----+----.----+----.----+  1140
TTAAAGAATTTAATTAATTATATAGAAATTTCTATAGTATAAAATACATACATCGAATAA n  f  l  n  .  l  i  y  l  .  r  y  h  i  l  c  m  .  l  i

----.----+----.----+----.----+----.----+----.----+----.----+

X                                N        A
              M                                L        L
              N                                A        U
              1                                3        1

CAAAGAAGTGTTTCCTATTTCTATATAGTTTATTATACATGATACTTGGGTAGCTCAACA
----.----+----.----+----.----+----.----+----.----+----.----+  1200
GTTTCTTCACAAAGGATAAAGATATATCAAATAATATGTACTATGAACCCATCGAGTTGT q  r  s  v  s  y  f  y  i  v  y  y  t  .  y  l  g  s  s  t

----.----+----.----+----.----+----.----+----.----+----.----+

↓                                                          ↓
 TM                                                         TM
 RS                                                         RS
 UE                                                         UE
 91                                                         91
 /                                                          /
TTCTTAATAAACAGCCTTTGTATTCAGAATATAAAATTGAAATAGATATATATAAAGTTA
----.----+----.----+----.----+----.----+----.----+----.----+  1260
AAGAATTATTTGTCGGAAACATAAGTCTTATATTTTAACTTTATCTATATATATTTCAAT f  l  i  n  s  l  c  i  q  n  i  k  l  k  .  i  y  i  k  l

----.----+----.----+----.----+----.----+----.----+----.----+

AAAAAAAAAAAAAAAAAA
----.----+----.--    1277
TTTTTTTTTTTTTTTTTT k  k  k  k  k  k

ANTIBODIES TO POLYPEPTIDES ENCODED BY ASPARTOACYLASE POLYNUCLEOTIDES

This application is a continuation of U.S. application Ser. No. 09/965,807, filed Oct. 1, 2001, now U.S. Pat. No. 7,217,547 which is a continuation of U.S. application Ser. No. 08/128,020 filed Sep. 29, 1993, now abandoned both of which are incorporated by reference herein.

BACKGROUND OF THE INVENTION

Canavan disease (CD), or spongy degeneration of brain, is an autosomal recessive leukodystrophy associated with mental retardation, megalencephaly, hypotonia and death, usually in the first decade of life. Brain histology in CD is characterized by spongy degeneration of white matter with astrocytic swelling and elongated mitochondria[1-5]. Canavan disease is more prevalent in Jewish people of Ashkenazi origin[3-5]. Matalon et al. (1988) described aspartoacylase deficiency as the basic biochemical defect in CD[6]. Since the initial report, 145 patients have been diagnosed with CD a single center, suggesting that CD is more prevalent than previously thought[10-12]. Aspartoacylase deficiency in CD has also been reported by other investigators[13,14].

The deficiency of aspartoacylase in CD leads to excessive excretion of NAA in urine and its accumulation in brain[6,9-11]. Aspartoacylase in brain has been localized to white matter associated with myelin tracks[16]. How aspartoacylase and the hydrolysis of NAA are involved in keeping white matter intact is not clear. It is also not understood how the deficiency of aspartoacylase leads to the pathogenesis seen in CD.

Aspartoacylase has been purified and characterized from bovine brain and from other bovine and human sources[16]. Biochemical and immunochemical studies suggest that aspartoacylase has been conserved during evolution. Aspartoacylase activity has been found in a variety of mammalian tissues, including kidney, brain white matter, adrenal glands, lung, liver and cultured skin fibroblasts. Brain grey matter and blood constituents do not have any detectable aspartoacylase activity (Kaul et al., unpublished studies).

Aspartoacylase specifically hydrolyses N-acetyl-L-aspartic acid (NAA) to aspartate and acetate[7,8]. Stereospecificity of aspartoacylase towards L-analog of NAA has been well documented. The D-analog of NAA acts as a weak inhibitor of NAA hydrolysis by aspartoacylase. Studies have suggested that the carbon backbone of NAA is involved in interaction with the substrate binding site of aspartoacylase; and that the substitutions at α and β carboxyl groups of aspartate moiety do not have any effect on hydrolysis of NAA by aspartoacylase[16].

The diagnosis of CD is now routinely made by quantitation of NAA in urine and estimation of aspartoacylase activity in cultured skin fibroblast[12]. The level of aspartoacylase activity found in direct chorionic villi cells or in cultured chorionic villi cells and amniocytes is about 2 orders of magnitude lower than that found in normal cultured skin fibroblasts. Due to the low aspartoacylase activity in chorionic villi cells and amniocytes, the prenatal diagnosis of CD using aspartoacylase assay is not satisfactory[15].

Due to the devastating nature of this genetic disease, there is an urgent need for better diagnostic methods for early detection of the disease, both pre- and postnatally, and screening methods to detect genetic carriers of the disease to allow informed genetic counseling for prospective parents. Additionally, there is a critical need for an effective treatment, and even more preferably, a cure for the underlying biochemical defect.

SUMMARY OF THE INVENTION

The present invention discloses the isolation and expression of human ASP cDNA, and thus provides the gene and protein encoded by the gene. In particular, the invention provides an isolated nucleic acid molecule comprising:
  (a) a nucleic acid sequence encoding a human aspartoacylase polypeptide;
  (b) a nucleic acid sequence complementary to nucleic acid sequence (a); or
  (c) a nucleic acid sequence at least 16 nucleotides in length capable of hybridizing, under stringent hybridization conditions, with one of said nucleic acid molecules (a) or (b).

More particularly, the invention provides a nucleic acid molecule described in (a), above, comprising:
  (i) a DNA molecule having the DNA sequence of FIG. 1 (SEQ ID NO: 1) from DNA position +1 to +891;
  (ii) a DNA molecule encoding a normal human aspartoacylase polypeptide having the amino acid sequence of FIG. 1 (SEQ ID NO: 1) from amino acid position +1 to +313;
  (iii) a DNA molecule having a sequence of a fragment of the DNA sequence of FIG. 1 (SEQ ID NO: 1), or a sequence complementary thereto, and including at least 16 sequential nucleotides;
  (iv) a DNA molecule having a sequence of a fragment of the DNA sequence of FIG. 1 (SEQ ID NO: 1) and including at least 16 sequential nucleotides, and which encodes a fragment of the amino acid sequence of FIG. 1 (SEQ ID NO: 1); or
  (v) a DNA molecule encoding an epitope of the amino acid sequence of FIG. 1 (SEQ ID NO: 1) between positions +1 to +313, and encoded by at least 18 sequential nucleotides.

In addition, the invention provides allelic or mutant versions of the above DNA molecules (i)-(v) wherein they are modified in at least one nucleotide position as compared with the sequence of FIG. 1 (SEQ ID NO: 1), corresponding to the sequence of a naturally-occurring allele of human aspartoacylase having an altered biological activity.

In another aspect, the invention provides an isolated normal aspartoacylase polypeptide capable of hydrolyzing N-acetyl-aspartic acid to aspartate and acetate. In particular, the invention provides a normal aspartoacylase polypeptide having the amino acid sequence of FIG. 1 (SEQ ID NO: 1) from amino acid position +1 to +313 as well as a mutant aspartoacylase polypeptide having either an altered ability of hydrolyze N-acetyl-aspartic acid to aspartate and acetate or incapable of hydrolyzing N-acetyl-aspartic acid to aspartate and acetate.

In another aspect of the invention, in view of the identification of a base change in the human ASP encoded aspartoacylase, which base change is present in 85% of Canavan alleles, the invention provides a means of identifying DNA sequences containing the mutation. Therefore, the invention additionally provides a means of diagnosing the disease in patients, and identifying carriers of the genetic defect. This aspect of the invention includes methods for screening a potential Canavan disease carrier or patient for the presence of an identified mutation and/or a different mutation in an aspartoacylase gene; for example:

hybridization assays, comprising (a) isolating genomic DNA from said potential Canavan disease carrier or patient, (b) hybridizing a DNA probe onto said isolated genomic DNA, said DNA probe spanning said mutation in said aspartoacylase gene, wherein said DNA probe is capable of detecting said mutation, (c) treating said genomic DNA to determine the presence or absence of said DNA probe and thereby indicating the presence or absence of said aspartoacylase mutation;

restriction fragment length polymorphism assays, comprising (a) isolating genomic DNA from said potential Canavan disease carrier or patient, (b) determining the presence or absence of a restriction endonuclease site in the gene, the presence or absence of which thereby indicates the presence or absence of said aspartoacylase mutation;

PCR assays, comprising (a) isolating genomic DNA from said potential Canavan disease carrier or patient, (b) determining the mobility of heteroduplex PCR products in polyacrylamide gels, the mobility of which thereby indicates the presence or absence of said aspartoacylase mutation; and immunoassays, comprising (a) providing a biological sample of the subject to be screened; and (b) submitting the sample to an assay for detecting in the biological sample the presence of a normal aspartoacylase gene, a mutant aspartoacylase gene, normal aspartoacylase polypeptide, mutant aspartoacylase polypeptide, or mixtures thereof.

In the above methods of screening (assays), either the presence of the normal or mutant aspartoacylase polypeptide or nucleic acid coding for said polypeptide can be detected. For each of the assays, kits are provided for carrying out the methods of the invention. These kits include nucleic acids, polypeptides and antibodies of the present invention, including fragments such as nucleic acid probes, oligopeptide epitopes and antibody fragments such as F(ab')$_2$ fragments.

In related aspects of the invention, genetic constructs and methods for making the nucleic acids, polypeptides and antibodies of the invention are provided, including cloning vectors, host cells transformed with cloning vectors and hybridomas; pharmaceutical preparations containing normal polypeptides for administering to patients to provide therapy to replace the mutant polypeptide; nucleic acid constructs suitable for administering to patients to provide a (preferably permanent) genetic therapy; methods for making the nucleic acids, polypeptides and antibodies of the present invention, including fragments such as nucleic acid probes, oligopeptide epitopes and antibody fragments such as F(ab')$_2$ fragments; and animals transformed with normal and mutant aspartoacylase genes to provide animal models for study of CD and related genetic diseases.

It will be appreciated by a skilled worker in the art that the identification of the genetic defect in a genetic disease, coupled with the provision of the DNA sequences of both normal and disease-causing alleles, provides the full scope of diagnostic and therapeutic aspects of such an invention as can be envisaged using current technology.

BRIEF DESCRIPTION OF THE DRAWINGS

Various other objects, features and attendant advantages of the present invention will be more fully appreciated as the same becomes better understood when considered in conjunction with the accompanying drawings, wherein:

FIG. 1 (SEQ ID NO: 1) depicts the nucleotide and predicted amino acid sequence of human ASP encoded transcript and protein. The cDNA is 1,435 bp and the initiator "atg" marks base 1 of coding sequence. The polyadenylation signal sequences are shaded. Also shown are the 18 base poly(A) tail. Amino acid sequence predicted from the human ASP cDNA is depicted as single letter code and initiator amino acid residue M is residue 1. There are several in frame termination codons present in human ASP cDNA upstream of the initiator atg codon. The potential N-glycosylation site is shown in bold type and marked by an asterisk (*). The numbers on left show amino acid residues while those on right are nucleotide base position.

Figure 3:
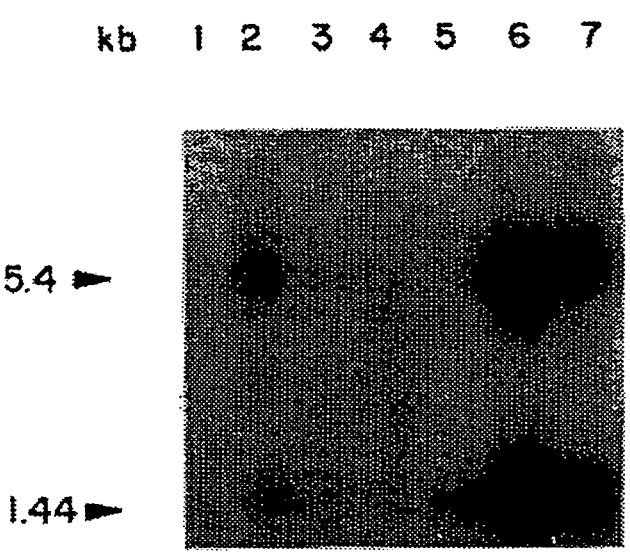

```
                                                                   SEQ ID NO: 1
         TTGTAACAGA AAATTAAAAT ATACTCCACT CAAGGGAATT CTGTACTTTG CCCTTTTGGT    -99

AAAGTCTCAT TTACATTTCT AAACCTTTCT TAAGAAAATC GAATTTCCTT TGATCTCTCT    -39

1                                        -1   M   T   S   C   H   I
         TCTGAATTGC AGAAATCAGA TAAAAACTAC TTGGTGAA ATG ACT TCT TGT CAC ATT     18

7      A   E   E   H   I   Q   K   V   A   I   F   G   G   T   H   G
            GCT GAA GAA CAT ATA CAA AAG GTT GCT ATC TTT GGA GGA ACC CAT GGG    66

23      N   E   L   T   G   V   F   L   V   K   H   W   L   E   N   G
            AAT GAG CTA ACC GGA GTA TTT CTG GTT AAG CAT TGG CTA GAG AAT GGC   114

39      A   E   I   Q   R   T   G   L   E   V   K   P   F   I   T   N
            GCT GAG ATT CAG AGA ACA GGG CTG GAG GTA AAA CCA TTT ATT ACT AAC   162

55      P   R   A   V   K   K   C   T   R   Y   I   D   C   D   L   N
            CCC AGA GCA GTG AAG AAG TGT ACC AGA TAT ATT GAC TGT GAC CTG AAT   210

71      R   I   F   D   L   E   N   L   G   K   K   M   S   E   D   L
            CGC ATT TTT GAC CTT GAA AAT CTT GGC AAA AAA ATG TCA GAA GAT TTG   258

87      P   Y   E   V   R   R   A   Q   E   I   N   H   L   F   G   P
            CCA TAT GAA GTG AGA AGG GCT CAA GAA ATA AAT CAT TTA TTT GGT CCA   306

103      K   D   S   E   D   S   Y   D   I   I   F   D   L   H   N*  T
            AAA GAC AGT GAA GAT TCC TAT GAC ATT ATT TTT GAC CTT CAC AAC ACC   354
```

-continued

```
119      T   S   N   M   G   C   T   L   I   L   E   D   S   R   N   N
         ACC TCT AAC ATG GGG TGC ACT CTT ATT CTT GAG GAT TCC AGG AAT AAC    402

135      F   L   I   Q   M   F   H   Y   I   K   T   S   L   A   P   L
         TTT TTA ATT CAG ATG TTT CAT TAC ATT AAG ACT TCT CTG GCT CCA CTA    450

151      P   C   Y   V   Y   L   I   E   H   P   S   L   K   Y   A   T
         CCC TGC TAC GTT TAT CTG ATT GAG CAT CCT TCC CTC AAA TAT GCG ACC    498

167      T   R   S   I   A   K   Y   P   V   G   I   E   V   G   P   Q
         ACT CGT TCC ATA GCC AAG TAT CCT GTG GGT ATA GAA GTT GGT CCT CAG    546

183      P   Q   G   V   L   R   A   D   I   L   D   Q   M   R   K   M
         CCT CAA GGG GTT CTG AGA GCT GAT ATC TTG GAT CAA ATG AGA AAA ATG    594

199      I   K   H   A   L   D   F   I   H   H   F   N   E   G   K   E
         ATT AAA CAT GCT CTT GAT TTT ATA CAT CAT TTC AAT GAA GGA AAA GAA    642

215      F   P   P   C   A   I   E   V   Y   K   I   I   E   K   V   D
         TTT CCT CCC TGC GCC ATT GAG GTC TAT AAA ATT ATA GAG AAA GTT GAT    690

231      Y   P   R   D   E   N   G   E   I   A   A   I   I   H   P   N
         TAC CCC CGG GAT GAA AAT GGA GAA ATT GCT GCT ATC ATC CAT CCT AAT    738

247      L   Q   D   Q   D   W   K   P   L   H   P   G   D   P   M   F
         CTG CAG GAT CAA GAC TGG AAA CCA CTG CAT CCT GGG GAT CCC ATG TTT    786

263      L   T   L   D   G   K   T   I   P   L   G   G   D   C   T   V
         TTA ACT CTT GAT GGG AAG ACG ATC CCA CTG GGC GGA GAC TGT ACC GTG    834

279      Y   P   V   F   V   N   E   A   A   Y   Y   E   K   K   E   A
         TAC CCC GTG TTT GTG AAT GAG GCC GCA TAT TAC GAA AAG AAA GAA GCT    882

295      F   A   K   T   T   K   L   T   L   N   A   K   S   I   R   C
         TTT GCA AAG ACA ACT AAA CTA ACG CTC AAT GCA AAA AGT ATT CGC TGC    930

311      C   L   H   .
         TGT TTA CAT TAG AA ATCACTTCCA GCTTACATCT TACACGGTGT CTTACAAATT     984

CTGCTAGTCT GTAAGCTCCT TAAGAGTAGG GTTGTGCCTT ATTCAACTGC ATACATAGCT  1044

CCTAGCACAG TGCCTTATTC GGTAGGCATC TAAGCAAATT TCTTAAATTA ATTAATATAT  1104

CTTTAAAGAT ATCATATTTT ATGTATGTAG CTTATTCAAA GAAGTGTTTC CTATTTCTAT  1164

ATAGTTTATT ATACATGATA CTTGGGTAGC TCAACATTCT T░░░░░CAG CCTTTGTATT   1224

CAGA░░░░░░ATTGAAATA GATATATATA AAGTTAAAAA AAAAAAAAAA AAA           1277
```

FIG. 2 depicts the alignment of human (HLASP) and bovine (BASPCON) ASP encoded protein sequence using the AALIGN program (Gap penalty 4, Deletion penalty 12, PAMfile STANDARD.PAM) in Lasergene software package from DNAstar (Madison, Wis.). The human and bovine aspartoacylase amino acid sequences share 92.3% identity in 313 aa overlap. Consensus amino acid sequence motifs predicted to be involved in catalytic center of aspartoacylase are shown as shaded areas. The potential N-glycosylation site is marked by an asterisk (*), and phosphorylation sites are highlighted as shadows.

FIG. 3 depicts an autoradiogram of Northern blot analysis of poly(A)+ RNA isolated from various human tissues. Two µg of poly(A)+ RNA from each tissue were fractionated on agarose gel and blotted on nylon membrane and blots were hybridized to human cDNA under stringent conditions. The human poly(A)+ RNAs are from; 1: heart, 2: brain, 3: placenta 4: lung, 5: liver, 6: skeletal muscle and 7: kidney.

Figure 4:
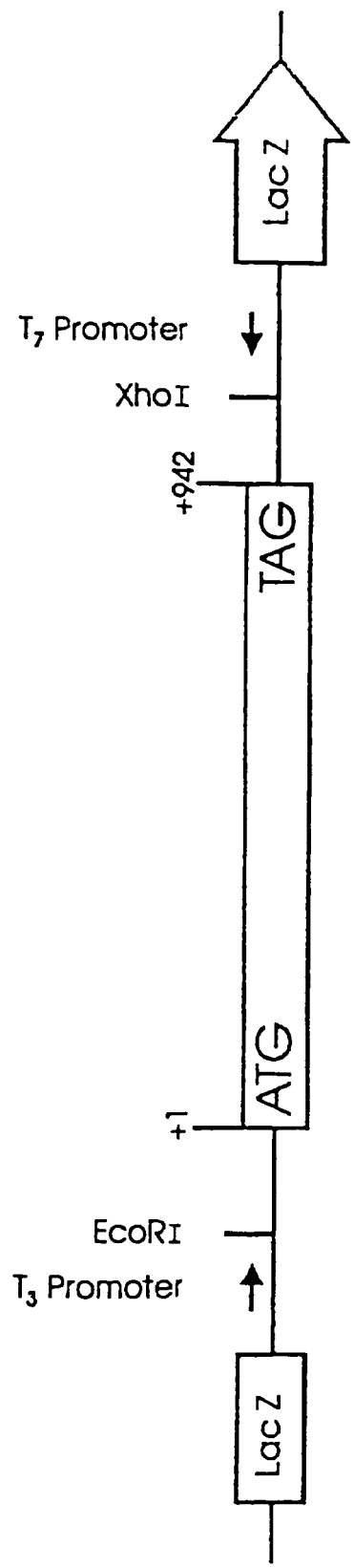

FIG. 4 depicts a schematic representation of pHLASP cloned in pBluescript SK−. The human ASP cDNA was cloned between Eco RI and Xho I sites in 5'→3' direction and the transcription was driven by LACZ promoter. The initiator "atg" and terminator "tag" codons are shown. Other vector regions are not represented in the schematics. The figure is not drawn to scale.

Figure 5A:
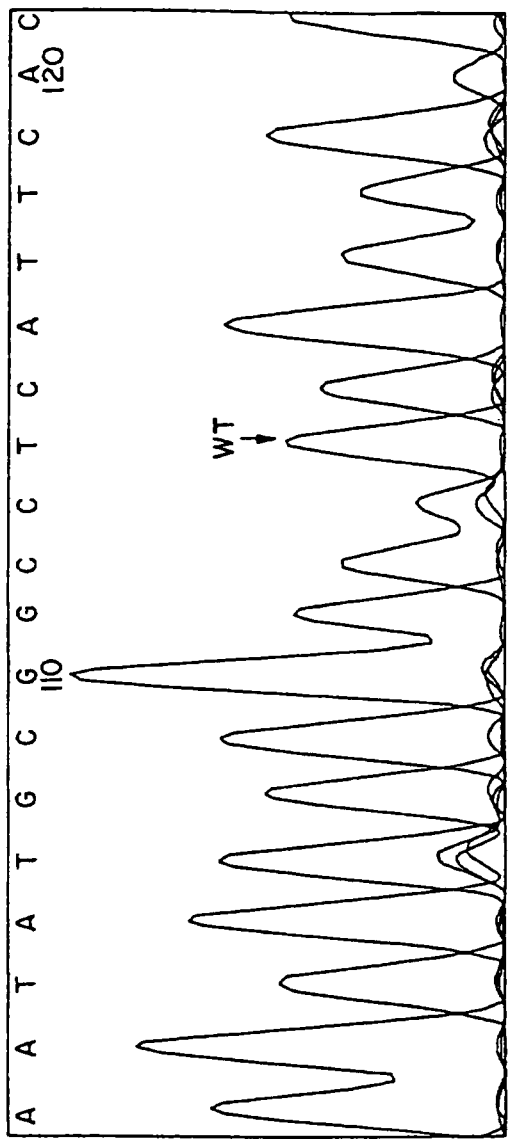
Figure 5B:
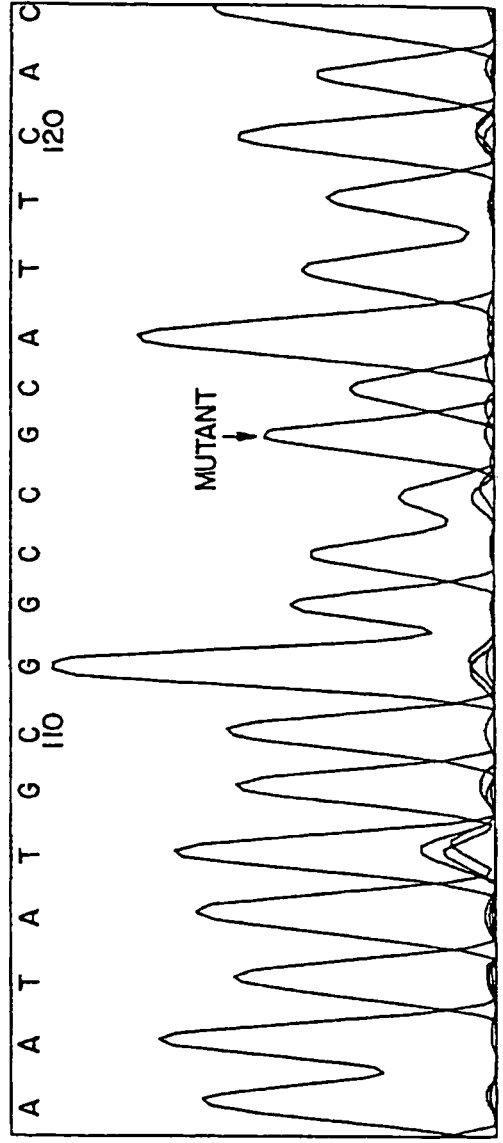

FIG. 5 depicts the nucleotide sequence of 312 bp cDNA fragment in the region of a854>c mutation from normal controls (WT, Panel A) and a patient with CD (MUT, Panel B). Reverse transcription of cytoplasmic RNA with HKRT1 (AACCCTACTCTTAAGGAC; SEQ ID NO: 5) primer was followed by amplification with HASP14F (F→CCGGGATGAAAATGGAGAA; SEQ ID NO: 6) and HASPC7R (R→ACCGTGTAAGATGTAAGC; SEQ ID NO: 7) primers. The prefix F and R in these oligos stand for M13 universal and reverse primer tags. Fluorescent di-deoxy sequencing of both strands were carried out with M13 universal and reverse primers. The patient with CD (MUT) was homozygous for a854>c point mutation and the base involved is shown by a down arrow (.dwnarw.). The mutation would result in E285>A missense mutation at the amino acid level.

FIG. 6 depicts the single strand conformation polymorphism (Panel A) and Eag I restriction endonuclease digestion (Panel B) of 237 bp cDNA fragment amplified by RT-PCR of cytoplasmic RNA from normal controls, and Canavan probands and their family members. After initial reverse transcription of cytoplasmic RNA with HKRT1 (AAC-CCTACTCTTAAGGAC; SEQ ID NO: 5) primer the 237 bp cDNA fragment was amplified using HASPG5 (AGGAT-CAAGACTGGAAACC; SEQ ID NO: 8) and HASPC7 (GTAAGACACCGTGTAAGA TG; SEQ ID NO: 9) primers. Representative SSCP and restriction digestion analysis of a854>c point-mutation in 3 families is shown and the pedigrees are drawn at the top. One of the normal controls (Lane 4) and the non-carrier sibling of a patient with CD (Lane 1) are also shown.

Figure 7D:
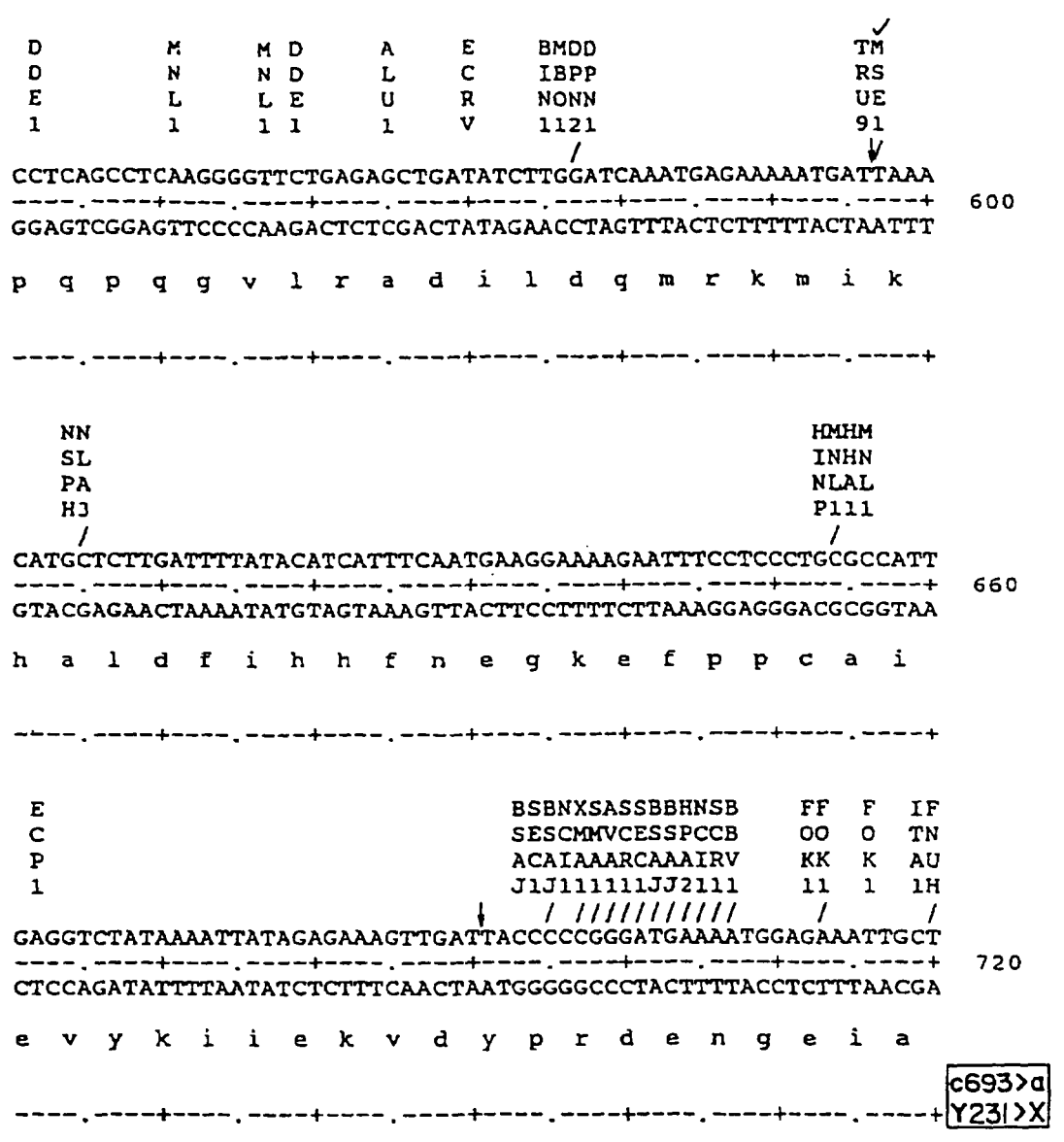

FIG. 7 is a restriction map of the structural gene sequences of ASP.

GENERAL DISCUSSION

The discovery of aspartoacylase deficiency and N-acetylaspartic aciduria has for the first time offered a definite diagnosis for CD without the need for brain biopsy (for review, see Matalon et al., 1993)[12]. The spongy degeneration of white matter in CD strongly suggests that hydrolysis of NAA by aspartoacylase plays a significant role in the maintenance of intact white matter.

Canavan disease is the only known genetic disorder which is caused by a defect in the metabolism of a small metabolite, NAA, synthesized exclusively in the brain[22,23] in a cell specific manner[24-26]. Since the initial discovery of NAA in brain[27], its biological role has remained unknown[28-32]. The stable level of NAA in brain has made it a useful marker in $^1$H NMR spectroscopy of brain (for review, see Birken and Oldendorf, 1989)[33]. Significantly reduced levels of NAA have been reported in non-CD focal or generalized demyelinating disorders[34], Huntington disease[35], HIV-seropositive individuals[36], acute stroke[37], myodystrophic mice[38] and mouse model of scrapie[39]. While such decrease in NAA level has been proposed as a measure of neuronal loss, it is not specific for any particular pathology. The accumulation of NAA, and dystrophy of white matter, in brain of patients with CD is highly specific and the elevated NAA level has been demonstrated both by biochemical and as well as $^1$H NMR spectroscopy of brain[9,10,16,34].

Aspartoacylase is present in a variety of tissues, and in most of the tissues tested, (Kaul et al., unpublished studies). Northern blot analysis has confirmed the expression of human ASP in the tissues tested so far. However, the enzyme seems to have a unique role in maintaining a homeostatic balance of NAA level, particularly in the white matter of brain. The disturbance of this equilibrium, as seen in CD, somehow leads to spongy degeneration of the white matter. The pathology seen in CD is apparently co-localized to the regions of brain that express aspartoacylase activity[16]. The grey matter, despite several fold increased levels of NAA[16], is spared of any significant pathological changes in CD. Without wishing to be bound by theory, it is believe that the critical role of NAA in brain function and biology is manifested through the action of aspartoacylase.

Since the pathology in CD is observed only in brain, it is suggested that aspartoacylase in tissues other than brain acts as scavenger of NAA from body fluids. The relative abundance of two human ASP transcripts is apparently regulated in a tissue dependent manner. The choice of polyadenylation site, and/or alternative splicing of pre-mRNA, as reason for the two transcripts is plausible. The polyadenylation signal or/and alternative splicing may provide an additional mode of regulating gene expression[20].

Hydrolysis of NAA by aspartoacylase is highly specific. N-Acetyl derivatives of amino acids other than aspartic acid are not hydrolyzed by aspartoacylase. In contrast, NAA is not hydrolyzed by aminoacylase I, an enzyme that hydrolyzes N-acetyl derivatives of all other amino acid, including N-acetyl-L-glutamic acid[7,8].

Human ASP encoded transcript and protein apparently do not share any homology with the human aminoacylase I cDNA.sup.21. Human and bovine aspartoacylase have sequences that have homology to the catalytic domain sequence motifs reported in esterases and other related hydrolytic enzymes.sup.19. The invariable amino acid residues histidine (H) and glutamic acid (E) involved in catalysis by esterases are present in the consensus sequence motifs GGTHGNE (SEQ ID NO: 10) and VNEAAYY (SEQ ID NO: 11) in aspartoacylase. The inhibition of aspartoacylase activity by diisopropyl fluorophosphate, (Kaul, unpublished data), further suggests that a serine (S) amino acid residue is involved at the active site. It is therefore proposed that aspartoacylase has an esterase-like activity and that its catalytic domain involves a triad of S, H and E amino acid residues. The E285 amino acid residue in wild type aspartoacylase is indeed part of the VXEXXXY (SEQ ID NO: 12) sequence motif involved in catalysis by esterases, and is conserved in bovine aspartoacylase. The substitution of the amino acid residue E with A residue should lead to the inactivation of aspartoacylase, as is observed in CD in patients with E285>A mutation.

The mutation data is based on a sample of 17 unrelated pedigrees of Ashkenazi Jewish descent. Since a854>c base change in ASP has not been observed in any of the 168 normal chromosomes analyzed, it supports the conclusion that this base change is indeed a mutation causing CD. The apparently predominant nature of a854>c point mutation, detected in 85% of the Canavan alleles, further suggests a founder effect of this mutation in the Jewish population. Such a predominant mutation can facilitate the study of epidemiology of CD in the population at risk. Mutation analysis can also be used for reliable screening for carriers of the genetic defect, as well as prenatal diagnosis.

In addition, two other mutations in the ASP gene have been identified which are also associated with Canavan disease:

One is a c693>a mutation, which results in the codon change TAC>TAA, which results in a translation error of Y231>X; thus, this mutation causes premature termination of the polypeptide chain at the location where a tyrosine residue is supposed to be. This is a "nonsense" mutation.

Another allele which has been identified is a c914>a change, which results in the codon change GCA>GAA, which in turn results in the missense mutation A305>E, substituting a glutamic acid for an alanine residue.

Thus, several mutations have been identified which are involved in Canavan disease, including a missense mutation which has been localized in the predicted catalytic domain of aspartoacylase, indicating the underlying genetic defect in the disease in the majority of patients. Therefore, the present invention also provides methods of treating and curing Canavan disease, comprising administering therapeutically effective amounts of a biologically active protein or a biologically active fragment thereof, or drugs which overcome the biological deficit caused by the genetic defect (the pharmacological approach), or administering therapeutically effective amounts of a nucleotide sequence coding for a biologically active protein or a biologically active fragment thereof, which nucleic acid allows the production of a biologically effective aspartoacylase protein in the affected cells (the genetic therapy approach).

In the disclosure which follows, it will be appreciated by the skilled worker that implementing the various utilities disclosed herein, as well as others, which can be derived from the provision of the DNA sequence for aspartoacylase of present invention, e.g., screening of carriers, diagnosis of disease and therapeutic applications, including polypeptide and gene therapies, are routinely achievable in view of the guidance of this disclosure, as well in view of conventional knowledge. Thus, the numerous routine protocols for conducting these various applications are also well known. Thus, for example, various other genes which are implicated in genetic defects are disclosed in the prior art, as are examples of various utilities for these other genes, and the genes, polypeptides, antibodies, etc., of the present invention, can be prepared analogously; similarly, the methods of the present invention can be conducted analogously.

DEFINITIONS

As used herein, "aspartoacylase" means the polypeptide coded for by the ASP gene, e.g., in humans. This definition thus includes the protein as isolated from human or animal sources, as produced by recombinant organisms and as chemically or enzymatically synthesized according to techniques routine in the art. This definition is understood to include the various polymorphic forms of the polypeptide wherein amino acid substitutions in the non-critical or variable regions of the sequence do not affect the essential functioning of the polypeptide or its secondary or tertiary structure. This definition includes the polypeptide which, in its normal condition, is present in non-Canavan disease patients or carriers and wherein it performs its normal functions.

As used herein, "mutant aspartoacylase" or "allelic variant of aspartoacylase" or "Canavan aspartoacylase" means the polypeptide coded for by an ASP gene which is highly analogous to aspartoacylase in terms of primary, secondary and tertiary structure, but wherein one or more amino acid substitutions, and/or deletions and/or insertions result in impairment of its essential function, so that organisms whose brain white matter cells express mutant aspartoacylase rather than normal aspartoacylase demonstrate one or more symptoms of Canavan disease.

As used herein, "Canavan disease" or "CD" refers to the genetic disease autosomal recessive leukodystrophy, defined above.

As used herein, "CD carrier" means a person in apparent health whose chromosomes contain a mutant ASP gene that may be transmitted to that person's offspring.

As used herein, "CD patient" means a person who carries a mutant ASP gene on both chromosomes on which the gene is carried, such that they exhibit the clinical symptoms of Canavan disease.

As used herein, "ASP gene" refers to the gene whose mutant forms are associated with Canavan disease. This definition is understood to include the various sequence polymorphisms that exist, wherein nucleotide substitutions in the gene sequence do not affect the essential function of the gene product. This term primarily relates to an isolated coding sequence, but can also include some or all of the flanking regulatory elements and/or any introns.

As used herein, "stringent hybridization conditions" are defined in accordance with what a skilled worker would understand such conditions to mean, depending on the nucleic acids being hybridized. Thus, stringent hybridization conditions for DNA-DNA hybrids are different from those for DNA-RNA heteroduplexes, and conditions for short (e.g., less than 200 and especially under 100 nucleotides in length) oligonucleotides are generally different than those for long sequences (≥200 nucleotides). Suitable conditions meeting the requirement of stringency are described in Reference 45. For example, for short oligonucleotide sequences, stringent conditions generally include hybridization at temperatures 5-10° C. below the $T_m$ for the specific sequence.

As used herein, "an aspartoacylase having altered biological activity" means an aspartoacylase polypeptide having a biological activity which, when expressed in vivo, results in phenotypic effects or symptoms of Canavan disease.

As used herein, "complementary" means a nucleic acid molecule has a sequence which complements a reference template sequence, whereby the two sequences can specifically hybridize. Preferably, the term refers to exact complementarity, e.g., as is found between the two strands of a nucleotide sequence in a naturally-occurring gene.

It will be understood by those of skill in the art that allelic or other sequence variations in the DNA and amino acid sequences of the ASP gene and its product aspartoacylase are included in the present invention. For example, allelic variants which result in aspartoacylase polypeptides having the identical amino acid sequence to the normal or most prevalent variant due to degeneracy of the genetic code are included. Further, allelic variants which result in aspartoacylase having essentially insignificant changes in the non-critical or variable regions of the polypeptide, e.g., not in regions of the polypeptide involved in the biological activity of the polypeptide such as is seen in Canavan disease, are also considered to be equivalents included in the scope of this invention. Such variants include those resulting in amino acid substitutions, e.g., as shown in Table 1, which provide a polypeptide having essentially the same function as the normal polypeptide. In each individual case, the equivalency can be determined by measuring the biological activity of the polypeptide in comparison with the normal polypeptide, e.g., according to the assay described in Reference 16. In contrast, it is more likely that sequence variations which occur inside the consensus sequences described below for esterase catalytic sites, which variations result in amino acid sequences not fitting the consensus sequence, will in turn result in a polypeptide with altered biological activity.

TABLE 1

Generally Equivalent Substitution of Amino Acids in a Polypeptide

| Original Amino Acid | Equivalent Amino Acid |
| --- | --- |
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

In general, the functions or the immunological identity may be significantly changed if substituents are selected which are less conservative than the amino acids shown in Table 1. Such significant changes can be achieved by substitutions with amino acids which differ more in their structure and in the functional groups. Significant changes are those having an effect on the three-dimensional structure, e.g., wherein the pleated sheet structure or the helical structure is affected. Also, interactions of the charged and the hydrophobic chains can be affected.

Mutations are defined by the homology of two polypeptides which are compared. The term "homology" comprises similar amino acids (for example, Table 1) and gaps in the sequences of the amino acids (homology=similarity). The polypeptides according to the invention have an amino acid sequence which has a homology of at least 80%, preferably 90%, more preferably 95% and most preferably 98% of the amino acid sequence of FIG. 1 (SEQ ID NO: 1).

As previously mentioned, the invention also comprises modifications of the DNA or cDNA. These modified sequences hybridize under stringent conditions with the DNA, which codes the protein according to the invention. The cDNA or DNA has a nucleotide sequence, which has a homology of at least 70%, preferably 80%, more preferably 90% and most preferably 95% with the cDNA or DNA sequence according to the FIG. 1 (SEQ ID NO: 1). The homology can be measured by hybridization, as it is described in R. Knippers, Molekulare Genetik (Molecular Genetics), 1982, Third Edition, Georg Thieme Verlag Stuttgart, New York.

The invention also includes polypeptides having posttranslational modifications, which are to be understood to mean changes which occur during or after translation. These include glycosylation, formation of disulfide bridges, and chemical modifications of the amino acids, for example, sulfation.

Glycosylation is a basic function of the endoplasmic reticulum and/or the Golgi apparatus. The sequence and the branching of the oligosaccharides are formed in the endoplasmic reticulum and changed in the Golgi apparatus. The oligosaccharides can be N-linked oligosaccharides (asparagine-linked) or O-linked oligosaccharides (serine-, threonine- or hydroxylysine-linked). The form of glycosylation is dependent on the host cell type and on the type from which the corresponding cell type is derived. The extent and the type of glycosylation can be affected by substances, for example as described in European publication EP 0 222 313. The variation of glycosylation can change the function of the protein.

Proteins often form covalent bonds within the chains. These disulfide bridges are produced between two cysteines, whereby the protein is specifically pleated. Disulfide bridges stabilize the three-dimensional structure of the proteins.

Methods for Isolating, Cloning and Expressing the ASP Gene

The methods used to isolate, clone and express the ASP gene disclosed in FIG. 1 (SEQ ID NO: 1) are outlined in Examples 1-6, below. However, it is evident to a skilled worker that, given the DNA sequence provided herein, many other means of isolating this gene and other related sequences, e.g., from other humans, including those having allelic variations of the sequence of FIG. 1 (SEQ ID NO: 1), e.g., from other libraries, including cDNA libraries from other human tissues as well as genomic libraries, from other species, including those from existing cDNA and genomic libraries as well as those which are commercially available or can be routinely constructed, e.g., according to methods well known in the art, e.g., according to the methods outlined in Sambrook et al.[45], are additionally made available. For example, probes synthesized in accordance with the DNA sequence in FIG. 1 (SEQ ID NO: 1) can be used to screen libraries constructed from the DNA isolated from other individuals or other species to find corresponding genes. In particular, given the conserved nature of the gene determined by sequence comparison with the bovine ASP gene, the almost ubiquitous presence of aspartoacylase in many tissue types tested thus far and the ubiquitous presence of NAA in other mammals, it is likely that many other animals contain an equivalent gene.

In general terms, the production of a recombinant form of aspartoacylase can be effected by a wide variety of procedures well known to those of ordinary skill in the art. In particular, the recombinant polypeptide can be produced following the procedures outlined in U.S. Pat. No. 5,227,292 for the neurofibromatosis type 1 gene and protein, especially from column 6, line 12 to column 8, line 2 and references cited therein (the disclosures of which are incorporated by reference herein), except that the procedures are conducted starting with a DNA encoding and aspartoacylase gene instead of an NF1 gene. Suitable promoters, control sequences, vectors, host cells, etc. are routinely determinable, e.g., as disclosed in WO 91/02796, directed to analogous methods for isolation, cloning and expressing the gene for cystic fibrosis, in particular, e.g., from page 95, line 28 to page 100, line 29 and the references cited therein. In particular it is noted that both normal and mutant polypeptides can be produced.

Thus, in view of the disclosure herein of the sequence for the aspartoacylase gene and suitable probes for the gene, aspartoacylase genes can be isolated from any suitable source and routinely be cloned into a suitable cloning vector, and ultimately into an expression vector, i.e., a replicable vector suitable for transforming a host cell and containing the aspartoacylase DNA sequence in operable linkage with suitable control sequences whereby the DNA sequence can be expressed. (Definitions of the terms used in this section, e.g., "operable linkage", "control sequences", etc., have their usual meanings, e.g., as described in U.S. Pat. No. 5,227,292, as well as in WO 93/06244.) The vector is then used to transform a suitable host cell and the host cell is cultured under suitable conditions to effect expression of the DNA sequence into the corresponding polypeptide. The expressed polypeptide is then isolated according to standard techniques well known in the art.

Methods for Isolating the Aspartoacylase Polypeptide

A method for isolating aspartoacylase from bovine brain is outlined in Reference 16, which isolation procedure is fully applicable to other aspartoacylase polypeptides from other tissues in which it is expressed. However, it is evident to a skilled worker, given the ability to produce the cloned aspartoacylase polypeptides in recombinant expression systems of the present invention, that purification from such expression systems can be performed analogously to other purifications from such sources, given the physicochemical properties of the polypeptide, e.g., properties which are revealed by its sequence as disclosed by the present invention, and the teaching of, e.g., Reference 16, as well as utilizing routine experimentation for optimization of results, e.g., yields and activity, from a particular source. For example, WO 91/02796 discloses methods for selecting purification techniques based upon the properties of the polypeptide. Other such techniques are well known in the art. For final purification of the polypeptide, many standard techniques can be utilized, e.g., ion exchange chromatography, gel permeation chromatography, adsorption chromatography or isoelectric focusing, immunoaffinity chromatography (see the discussion regarding preparation of antibodies to aspartoacylase), preparative polyacrylamide gel electrophoresis, and high performance liquid chromatography (HPLC).

The homogeneity of the thus-produced aspartoacylase can be determined using standard protein analytical techniques. See, e.g., Sambrook et al.[45]

Preparation of Antibodies to Aspartoacylase

The present invention also provides antibodies which selectively bind to epitopes of aspartoacylase. These antibodies can be produced according to well known techniques in the art, including immunization of suitable antibody-producing animals with whole aspartoacylase polypeptides (including the mutant forms of aspartoacylase) or immunologically-effective fragments thereof, e.g., epitopes, to provide polyclonal antibodies to the polypeptide. Preferably, the antibodies are high affinity antibodies, e.g., having affinities, i.e., dissociation constants, of $10^{-6}$, more preferably $10^{-7}$, $10^{-8}$, $10^{-9}$ or higher. In addition, according to well known techniques such as, e.g., Kohler and Milstein[49], monoclonal antibodies to epitopes of aspartoacylase can also be produced. Still further, antibody fragments, such as $F(ab')_2$ fragments, can be produced and used according to well known methods.

These antibodies or antibody fragments can be used for a variety of purposes. For example, they can be used to purify aspartoacylase from solutions, e.g., fractionated cell supernatants or media containing secreted aspartoacylase from host cells containing the clones gene in an expressible, secreted form. Additionally, the antibodies, or fragments thereof, can be used in a wide variety of immunological assays for the detection of aspartoacylase and its mutants. Thus, these antibodies can be used in the immunoassay-based screening and diagnostic methods of the present invention.

Treatment by Administration of Functional ASP Protein or Fragments Thereof

In a pharmacological approach, treatment of Canavan disease can be performed by replacing the defective aspartoacylase polypeptide with normal polypeptide, by modulating the function of the defective polypeptide or by modifying another step in the pathway in which aspartoacylase participates in order to correct the physiological abnormality.

To be able to replace the defective polypeptide, reasonably large amounts of pure aspartoacylase must be available. Pure aspartoacylase can be obtained as described above from cultured cell systems, e.g., containing cloned and expressed ASP gene. Delivery of the polypeptide to the affected white matter requires its packaging and administration by means which allows the intact polypeptide to cross the blood-brain barrier, e.g., by disrupting the barrier, thereby allowing the polypeptide to pass through it, e.g., according to the methods outlined in U.S. Pat. No. 4,866,042 and references cited therein, or by encapsulating the polypeptide in, e.g., liposomes, whereby the barrier can be crossed without disruption, e.g., according to the methods outlined in WO 91/04014 and references cited therein. Other techniques known in the art for delivery to the affected situs can also be used.

Suitable amounts of polypeptide and regimens of administration, including routes and frequency of administration, for treatment of Canavan disease can be routinely determined by the skilled practitioner. For example, an effective dosage for treatment of a patient who has been diagnosed with Canavan disease will be 0.1 to 100 U/kg, more preferably 0.5 to 60 U/kg, still more preferably 1 to 20 U/kg, most preferably 2 to 10 U/kg of body weight/day, or twice weekly, and which will be optimized for the individual patient, e.g., in analogy with administration of glucocerebrosidase for treatment of Gaucher disease. Optimization of dosage can be determined by monitoring clinical symptoms, as well as measuring the levels of NAA in various body tissues. For example, NMR spectroscopy of the brain can be used to monitor NAA levels in vivo. Effective dosages are those which substantially alleviate the clinical manifestations of Canavan disease.

The aspartoacylase polypeptide can be formulated in conventional ways standard in the art for administration of protein substances. Administration by injection with a pharmaceutically acceptable carrier or excipient, either alone or in combination with another agent, is preferred. Suitable formulations include solutions or suspensions emulsions or solid compositions for reconstitution into injectables. Acceptable pharmaceutical carriers are those which dissolve the aspartoacylase polypeptide or hold it in suspension and which are not toxic to the extent of permanently harming the patient. Those skilled in the art will know, or be able to ascertain with no more than routine experimentation, particular suitable pharmaceutical carriers for this composition. See, for example, the protocols disclosed in U.S. Pat. No. 5,227,292 (see, e.g., column 12, line 1-68).

Treatment by Genetic Therapy

In a preferred therapeutic aspect of the present invention, patients suffering from Canavan disease are provided with a permanent source of normal aspartoacylase polypeptide, i.e., by way of provision of a normal ASP gene, at the appropriate site(s) in the body to partially, substantially or totally relieve the deleterious effects of the genetic defect in the mutant ASP gene. Such somatic gene therapy has been shown to be effective for a number of genes involved in genetic defects. For example, adenosine deaminase deficiency disease has been cured by administration of a normal gene for the defective enzyme. Similarly, the gene coding for aspartoacylase is provided to patients in need of such treatment, i.e., patients suffering from Canavan disease, whereby the deleterious effects of the defective mutant gene are relieved.

Various options are available for effecting genetic therapy, including but not limited to somatic gene therapy at the affected site, e.g., administering a therapeutically effective dosage of the gene to tissues and/or cells in which the gene is needed to prevent disease; whole body somatic therapy, whereby most if not all tissues and/or cells in the body receive a therapeutically effective dosage of the gene, whether or not the disease is manifested in that tissue or cell; and germ line gene therapy, wherein the genetic defect is cured in the reproductive cells of the carrier or patient, whereby that person will only transmit normal and not defective alleles to his or her children.

The preferred gene therapy method for Canavan disease will vary with the patient or carrier to be treated, and can be determined using no more than routine experimentation by the skilled practitioner. In particular, guidance a gene therapy techniques and considerations are disclosed in the series Human Gene Therapy[50]. Introduction of the DNA coding for the normal aspartoacylase into cells in need of this treatment can be through the use of retroviral vectors, non-retroviral vectors such as adenoviral vectors, vaccinia virus herpesvirus, or animal virus vectors such as Moloney murine leukemia virus and SV40 virus. Protocols for such gene therapy are disclosed in WO 91/02796 (page 106, line 15-page 108, line 9), as well as those disclosed in WO 92/10564 and WO 90/11092. Particular protocols can be optimized as needed.

The methods of delivery of the genetic therapeutic material to a particular location, e.g. the white matter of the brain, are also disclosed in the various references cited herein, and in particular in U.S. Pat. No. 4,866,042 and references cited therein, and in WO 91/04014 and references cited therein.

Other Treatments

Other treatment regimes can also be facilitated by the present invention. For example, drug therapy providing modulation of the defective aspartoacylase can be developed by using screening methods made possible by the present invention. Cultured cell systems expressing the defective aspartoacylase polypeptide can be used to screen drugs for their effectiveness in vitro for improving the performance of the defective polypeptide. Alternatively, drugs can be designed based upon the disclosed structure of the polypeptide to compensate for the defective structure of the mutant polypeptide. Still further, drugs could be developed which modulate the stability or production of the defective polypeptide in order to compensate for the decreased activity of the mutant polypeptide. These alternatives are discussed in detail in WO 91/02796 with respect to the cystic fibrosis polypeptide, which discussion is fully applicable herein to the aspartoacylase polypeptide.

In addition, the present invention facilitates the development of therapies based on modulation of the amounts of substrate and/or end products of the reaction catalyzed by aspartoacylase. For example, acetate and/or aspartic acid and/ or their further metabolites may be administered to compensate for the lack of production of these products, including their further metabolic products, e.g., analogously to the administration of L-DOPA to compensate for the deficiency of tyrosine hydroxylase in Parkinsonism. Alternatively, if the clinical symptoms are caused by excessive buildup of NAA, compounds can be administered to bind, e.g, chelate, NAA, or to competitively inhibit its binding at sites where such binding is causing the clinical symptoms, e.g., analogously to administration of dopamine antagonists in the treatment of amphetamine and drug abuse.

Production of Probes and Primers

Various aspects of the present invention require the use of nucleotide probes and primers which hybridize with nucleic acid sequences of the aspartoacylase gene. Given the sequence of that gene provided herein, it is routine for such molecules to be prepared. See, e.g., the manufacturer's instructions which accompany various commercial PCR amplification equipment and kits (e.g., those of Perkin Elmer Cetus), or nucleic acid synthesizers (e.g., those of Applied Biosystems, Inc., Foster City, Calif.).

Design and selection of suitable probes and primers is routine for the skilled worker. For example, suitable probes for detecting a given mutation include the nucleotide sequence at the mutation site and encompass a sufficient number of nucleotides to provide a means of differentiating a normal from a mutant allele. Suitable probes include those complementary to either the coding or noncoding strand of the DNA. Similarly, suitable PCR primers are complementary to sequences flanking the mutation site. Production of these primers and probes can be carried out in accordance with any one of the many routine methods, e.g., as disclosed in Sambrook et al.[45], and those disclosed in WO 93/06244 for assays for Goucher disease.

In general, suitable probes and primers will comprise, at a minimum, an oligomer at least 16 nucleotides in length, since, as disclosed in Reference 45 (page 11.7), calculations for mammalian genomes indicate that for an oligonucleotide 16 nucleotides in length, there is only one chance in ten that a typical cDNA library (complexity$\approx 10^7$ nucleotides) will fortuitously contain a sequence that exactly matches the sequence of the nucleotide. Therefore, suitable probes and primers corresponding to epitopes are generally 18 nucleotides long, which is the next larger oligonucleotide fully encoding an amino acid sequence (i.e., 6 amino acids in length).

Methods of Pre- and Postnatal Diagnosis and Carrier Screening

By use of nucleotide and polypeptide sequences provided by the present invention, safe, effective and accurate testing procedures are also made available to identify carriers of mutant alleles of aspartoacylase, as well as pre- and postnatal diagnosis of fetuses and live born patients carrying either one or two mutant alleles. This affords potential parents the opportunity to make reproductive decisions prior to pregnancy, as well as afterwards, e.g., if chorionic villi sampling or amniocentesis is performed early in pregnancy. Thus, prospective parents who know that they are both carriers may wish to determine if their fetus will have the disease, and may wish to terminate such a pregnancy, or to provide the physician with the opportunity to begin treatment as soon as possible, including prenatally. In the case where such screening has not been performed, and therefore the carrier status of the patient is not known, and where Canavan disease is part of the differential diagnosis, the present invention also provides a method for making the diagnosis genetically, without resort to brain biopsy.

Many versions of conventional genetic screening tests are known in the art. Several are disclosed in detail in WO 91/02796 for cystic fibrosis, in U.S. Pat. No. 5,217,865 for Tay-Sachs disease, in U.S. Pat. No. 5,227,292 for neurofibromatosis and in WO 93/06244 for Goucher disease. Thus, in accordance with the state of the art regarding assays for such genetic disorders, several types of assays are conventionally prepared using the nucleotides, polypeptides and antibodies of the present invention. For example:

Genetic screening: Biological samples containing nucleic acids can be evaluated using a variety of nucleic acid-specific techniques:

1. Direct sequencing: The DNA from an individual can be cloned, whereby both alleles are cloned. They can then be evaluated for differences in their nucleic acid sequence from normal alleles by direct sequencing of the individual's aspartoacylase gene.

2. Heteroduplex analysis: RNA transcripts can be made from a standard cloned gene, either the normal or mutant gene, and then hybridized with DNA from the individual and the resulting heteroduplex treated with RNase A and run on a denaturing gel to detect the location of any mismatches.

3. Restriction Fragment Length Polymorphism (RFLP): Restriction enzymes can be used which provide a characteristic pattern of restriction fragments, wherein a restriction site is either missing or an additional restriction site is introduced in the mutant allele. Thus, DNA from an individual and from control DNA sequences are isolated and subjected to cleavage by restriction enzymes which are known to provide restriction fragments which differentiate between normal and mutant alleles, and the restriction patterns are identified. While this assay is very simple, it is limited by the requirement that the mutation being tested for is known in advance.

4. Single Strand Conformation Polymorphism (SSCP): This is a rapid and sensitive assay for nucleotide alterations, including point mutations. See Reference 42. DNA segments 100-400 bp in length are amplified by PCR, heat denatured and electorphoresed on high resolution, non-denaturing acrylamide gels. Under these conditions, each single-stranded DNA fragment assumes a secondary structure determined in part by its nucleotide sequence. Even single base changes can significantly affect the electrophoretic mobility of the PCR product.

5. Polymerase Chain Reaction (PCR): This powerful technique can be used to test very small amounts of DNA from an individual, by amplifying DNA sequences in the region flanking the portion of the aspartoacylase gene known to be involved in a given mutation. Sequencing or other analysis of the amplified sequences is thereby simplified.

Polypeptide Screening:

1. Enzymatic activity: Biological samples from the individual to be tested e.g., taken from tissues in which detectable levels of aspartoacylase are normally produced, are assayed for the presence of aspartoacylase. It is noted that brain samples are not required, even though the effects of the mutant gene are most profound in white matter. The presence or absence of an enzymatically effective aspartoacylase can then be detected according to the assay outlined in Reference 16.

2. Immunoassay: Antibodies can be produced which are specific for either or both normal or mutant aspartoacylase, according to methods outlined above. Biological samples from the individual to be tested are then assayed, e.g., taken from tissues in which detectable levels of aspartoacylase are normally produced. It is noted that brain samples are not required, even though the effects of the mutant gene are most profound in white matter. A variety of immunoassays can then be performed on the samples, using a variety of detection methods, to detect the presence or absence of the mutant gene product.

Details of protocols for performing these screening techniques are well known in the art, and are exemplified in WO 91/02796 and references cited therein, as well as U.S. Pat. No. 5,217,865, which details analogous techniques for screening for Tay-Sachs disease, which, coincidentally, is a genetic disease also present in the Ashkenazi Jewish population. Therefore, assay methods and kits are also provided which can be used to simultaneously screen for these two, as well as other, genetic diseases.

Animal Models for Canavan Disease

The creation of a mouse or other animal model for Canavan disease is crucial to a full understanding of the disease and to test possible therapies (for a review of creating animal models, see Erickson[51]). Currently, no animal model of Canavan disease exists. The evolutionary conservation of the aspartoacylase gene as demonstrated by the sequence homology with the bovine gene indicates that an orthologous gene is likely to exist in the mouse, which can be identified using human or bovine aspartoacylase sequences as probes. Thereby, generation of a specific mutation analogous to the Canavan allele can be effected to reproduce the disease phenotype, as well as other mutations, including complete inactivation of the mouse gene, in order to study the biochemistry, molecular biology and physiology of the polypeptide.

For making such animal models, the various methods disclosed in WO 91/02796 can be adapted for the aspartoacylase gene with only routine experimentation.

Thus, in addition to providing materials for screening, treatments and diagnoses, the present invention provides materials which are useful as research tools, e.g., in order to further investigate basic questions regarding the role of aspartoacylase in Canavan disease, as well as other genetic disease caused by, e.g., mutations in enzymes, in particular esterases, as well as the role of NAA hydrolysis by aspartoacylase in the disease and lead to better management of patients with CD.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above and below, if any, are hereby incorporated by reference; the attached appendices are a part of this specification, and references cited therein are also hereby incorporated by reference.

EXAMPLES

Part I: Materials and Methods

Example 1

Materials, Reagents and Bacterial Strains

The materials and reagents used in the study were: Immobilon PVDF transfer membrane (Millipore, Bedford, Mass.); restriction enzymes (IBI, New Haven, Conn.; New England Biolabs, Beverly, Mass., Promega, Madison, Wis. and Boehringer Mannheim, Indianapolis, Ind.); Gene Amp RNA PCR kit and AmpliTaq PCR kit for amplification of DNA (Perkin-Elmer Cetus, Norwalk, Conn.); Random primed DNA labeling kit (Boehringer Mannheim, Indianapolis, Ind.); α-[$^{32}$P]-dNTP's, 3000 Ci/mMole (NEN/Dupont, Wilmington, Del.); RNAzolB kit for preparation of cytoplasmic RNA from cultured cells (Biotecx, Houston, Tex.); Biodyne Nylon membranes for Southern and Northern blots (Pall Biosupport, East Hills, N.Y.); nitrocellulose membranes for screening libraries (Schleicher & Schuell, Keene, N.H.); and Taq Dye primer and Taq dye-terminator cycle sequencing kits for fluorescent labeled automated DNA sequencing (Applied Biosystems, Foster City, Calif.). λUni-Zap (host strain XL1 Blue) human lung cDNA library and pBS(+) and pBluescript SK$^-$ phagemid vectors were from Stratagene (La Jolla, Calif.); λgt11 (host strain Y1090) human kidney and bovine lung cDNA libraries; λEMBL-3A Sp6/T7 (host strain LE 392) bovine genomic library; and poly(A)$^+$ RNA were from Clontech (Palo Alto, Calif.).

Example 2

Determination of the Amino Acid Sequence of Bovine Aspartoacylase Peptides

The amino terminal sequence of bovine brain aspartoacylase could not be obtained due to the autolysis of purified protein during storage. Purified aspartoacylase was digested with cyanogen bromide.sup.40 and peptides were fractionated on a 16.times.100 mm Mono Q column (FPLC system, Pharmacia LKB). Peptides were eluted with a 0-30% linear gradient of 1 M sodium chloride in buffer A (25 mM Tris.Cl pH 7.2 and 0.1% sodium azide), at a flow rate of 2 ml/min. The amino acid sequences of four peptides determined at a protein sequencing facility (Yale University, New Haven, Conn.) were as follows:

```
                                          (SEQ ID NO: 13)
CN8.1:   LENSTEIQRTGLEVKPFITNPRAVKK;

(SEQ ID NO: 14)
CN8.2:   KPLIPXDPVFLTLDGKTISLGGDQTXYPXFXNEAAYY;

(SEQ ID NO: 15)
CN30:    XKVDYPRNESGEISAIIHPKLQDQ;
and (SEQ ID NO: 16)
CN41:    XXXALDFIXNFXEXKE.
```

Example 3

Preparation of Oligonucleotides; Reverse Transcription; PCR Amplification; DNA Probes Oligonucleotides were synthesized by phosphoramidite chemistry on a 380B DNA Synthesizer (Applied Biosystems, Foster City, Calif.). First strand cDNA was synthesized by reverse transcription of 20 ng of Poly(A)+ RNA or 4 μg of cytoplasmic RNA with either oligo(dt)$_n$ or a gene-specific primer under standard conditions suggested by the manufacturer. DNA amplification[41] was carried out in DNA Thermal cycler Model 9600 (Perkin-Elmer Cetus, Norwalk, Conn.). Specific DNA sequences were amplified in 100 μl volumes with 20 ng of cloned or 500 ng of genomic DNA template according to the standard conditions suggested by the manufacturer. The PCR conditions were: 1 cycle of denaturation at 94° C. for 3 min, annealing for 30 sec at temperatures ($T_m$–4° C.) that were primer-dependant and extension at 72° C. for 1 min; followed by 27 cycles of denaturation at 94° C. for 30 sec, annealing for 30 sec and extension at 72° C. for 30 sec. The last step was extension at 72° C. for 7 min. The tubes were chilled to 4° C. until further analysis. For SSCP[42] and restriction digestion analysis of mutant alleles, PCR was carried out similarly except that 1 μCi of α-[$^{32}$P] dCTP was included in the PCR reaction mixture.

Small DNA fragments of less than 200 bp were labeled with $^{32}$P by PCR amplification of the desired DNA sequences using α-[$^{32}$P] dNTP's. DNA fragments bigger than 200 bp were labeled by the random primer method[43] following the conditions suggested by the manufacturer. The specific activities of probes were 3-5×10$^8$ cpm/μg DNA.

Example 4

Isolation of cDNA Clone, and Determination and Analysis of the Nucleotide Sequence The first strand bovine cDNA was synthesized by reverse transcription (RT) of bovine kidney poly(A)+ RNA with oligo (dt)$_{20}$. The bovine aspartoacylase-specific coding sequences were amplified by polymerase chain reaction (PCR) using first strand cDNA as the template and CN30 peptide-based primers
CD5 (AAA/GGTIGAC/TTAC/TCCIIGIAA;) and
CD8 (TGA/GTCC/TTGIAIC/TTTIGGA/GTG).

The cDNA fragment thus amplified was 69 bp long, which is the size expected from the CN30 peptide. The ORF of this fragment predicted the amino acid sequence of CN30 peptide. The 69 bp fragment was used as a probe to screen .lamda.gt11 bovine lung cDNA library. One cDNA clone, .lamda.ABL2, was isolated. The insert in .lamda.ABL2 had a single 839 bp long ORF. The amino acid sequence predicted by the ORF of .lamda.ABL2 insert contained the CN8.1, CN8.2, CN30, and CN41 peptide sequences described earlier. However, the cDNA clone was truncated at the 5' and 3' termini. The sequences downstream of the 3' termini of .lamda.ABL2 insert were cloned by RT-PCR amplification of bovine kidney poly(A).sup.+RNA using oligo(dt).sub.20 and the bovine aspartoaqase cDNA specific primer CD48-1 (CCGTGTAC-CCAGTGTT; SEQ ID NO: 19).
A unique 770 bp fragment was amplified that overlapped with the 3' sequence of λABL2 insert. The insert from λABL2 was used to screen bovine liver genomic library cloned in λEMBL3A vector according to the standard conditions[44,45]. Limited nucleotide sequence of genomic clones identified the missing 5' coding and non-coding sequences of bovine aspartoacylase cDNA.

Bovine cDNA (data not presented), was next used for isolation of human ASP cDNA clones. Human cDNA libraries were screened and the isolated clones analyzed by the methods described earlier or according to the standard protocols[44,45]. The human lung aspartoacylase cDNA was rescued from λUni-Zap human lung cDNA clone by co-transfection with helper phage R408 into XL-1 Blue strain of *E. coli* according to the protocol suggested by the manufacturer. The rescued recombinant pHLASP was transfected into *E. coli* (XLI Blue strain). Large scale recombinant phagemid DNA were purified on cesium chloride gradients[45].

The nucleotide sequence of double stranded plasmid and amplified DNA fragments was determined by the dideoxy chain termination method[46]. M13 universal/reverse and T3/T7 primers, or dideoxy NTP's, tagged with fluorescent dyes, were used for sequencing both strands of DNA fragments on an automated 373A DNA sequencer (Applied Biosystems, Foster City, Calif.). Fluorescent DNA sequencing was carried out with DNA sequencing kits and used according to the protocols suggested by the manufacturer.

Sequences were analyzed with Lasergene software package for DNA analysis from DNAstar (Madison, Wis.).

Example 5

Analysis of RNA

Cytoplasmic RNA was prepared from cultured cell lines[47] using a RNAZOL B kit for isolation of RNA (Biotecx, Houston, Tex.). Two to three μg of poly(A)+ RNA and 4.5 μg of RNA markers (Promega) were denatured with formamide. The denatured RNA was fractionated on a 1% agarose gel in formaldehyde containing buffer. The RNA was transferred overnight onto a nylon membrane. The blots were baked in a vacuum oven at 80° C. for 90 min, hybridized, and then washed under stringent conditions and autoradiographed[45].

Example 6

Expression of Aspartoacylase by Human Asp cDNA Clone pHLASP

The *E. coli* (XLI Blue strain) transformed with recombinant pHLASP or wild type pBluescript SK⁻ phagemid were grown overnight in 15 ml of Luria broth containing glucose (0.1%) and ampicillin (50 μg/ml) in the absence or presence of 20 mM IPTG. The bacteria were harvested, treated with 500 μL of 0.05 mg/ml lysozyme in 25 mM Tris.Cl pH 8.0, 10 mM EDTA and 50 mM glucose for 10 min at ambient temperature. The treated bacteria were diluted with ice cold 1.5 ml of 50 mM Tris.Cl, pH 8.0, 0.01% β-mercaptoethanol and 0.01% sodium azide and sonicated by three 10 sec bursts in ice cold conditions. The protein concentration in the bacterial sonicates was determined[48]. Aspartoacylase assays were carried out in duplicate with 450 μg protein of bacterial sonicate under standard incubation conditions described elsewhere[16]. Controls lacking substrate or enzyme during the incubation were run simultaneously to account for background absorption in each assay. One mU of enzyme activity is defined as 1 nanomole of aspartate released/min of incubation time.

Example 7

Mutation Analysis

Cytoplasmic RNA (4 μg) from cultured fibroblast of normal controls, probands and their family members was reverse transcribed with
HKRT1 (AACCCTACTCTTAAGGAC; SEQ ID NO: 5).
Aspartoacylase specific coding sequences were amplified by PCR with
HASP9 (CTTCTGAATTGCAGAAATCA; SEQ ID NO: 20) and HASPC7 (GTAAGACACCGTGTAAGATG; SEQ ID NO: 21)
primers. The full length coding sequence thus amplified was used as template to amplify 200 to 300 bp overlapping cDNA fragments and nucleotide sequence was determined. For a854>c point mutation analysis, a 312 bp fragment was amplified with
HASP14F (F→CCGGGATGAAAATGGAGAA; SEQ ID NO: 6) and
HASPC7R (R→ACCGTGTAAGATGTAAGC; SEQ ID NO: 7)
primers. The prefix F and R in these oligos stand for M13 universal and reverse primer tags, that allowed determination of nucleotide sequence using fluorescent tagged M13 primes.

For SSCP and restriction digestion analysis, the 237 bp cDNA fragment with a854>c mutation was amplified in presence of $\alpha$-[$^{32}$P] dCTP using
HASPG5 (AGGATCAAGACTGGAAACC; SEQ ID NO: 8) and
HASPC7 (GTAAGACACCGTGTAAGATG; SEQ ID NO: 9)
primers. The analysis for SSCP in the 237 bp amplified cDNA fragments was carried out in 40 cm long, 5% polyacrylamide gels in 1×TBE and 5% glycerol[42]. Electrophoresis was carried out at 7.5 Watts at ambient temperature for 16-18 h, and the gel was autoradiographed. The a854>c mutation was also analyzed by restriction digestion of 237 bp cDNA fragment with Eag I or Not I. Following electrophoresis of the digest on native 5% polyacrylamide gels in 1.times.TAE, the gel was autoradiographed.

Part II: Results

Example 8

Isolation and Characterization of Human ASP cDNA

Human aspartoacylase specific coding sequences were amplified by RT-PCR of human kidney poly(A)$^+$ RNA using oligo (dt)[16] for first strand cDNA synthesis followed by PCR using bovine cDNA-based primers
CD56I (GGG/ATAIACIGTT/CTGG/ATCICCICC) and
CD59I (CCIA/CGIGCIGTIAAA/GAAA/GTG) (data not shown).

A specific 676 bp cDNA fragment was amplified and found to have 90% identity to the corresponding region of the bovine ASP cDNA. The 676 bp partial human cDNA was used as probe to screen human lung .lamda.Uni-Zap and human kidney .lamda.gt11 cDNA libraries. This resulted in the isolation of several overlapping clones. Three of the clones with largest insert of 1.45 kb, also had identical terminal sequences. One of these, .lamda.gt11 HK5-1 was isolated from human kidney library and two clones .lamda.Uni-Zap HL 1 and two were isolated from the human lung library. The recombinant pHLASP was excised from .lamda.Uni-Zap HL1 clone. The nucleotide and the predicted amino acid sequence of pHLASP is shown in FIG. 1 (SEQ ID NO: 1).

The human ASP cDNA is 1,435 bp with 158 bp 5' and 316 bp 3' untranslated sequence. The isolated cDNA has 18 bases long poly(A) tail. A polyadenylation signal "aataaa" is found 48 bases upstream from the poly(A) addition site. Another consensus polyadenylation signal sequence "tataaa" is present 23 bases upstream from the poly(A) addition site. The position of "tataaa" is within the suggested location of 10-30 bases upstream from the poly(A) addition site[17,18]. Human and bovine ASP encoded transcripts and proteins do not match any known sequences in the databases.

The open reading frame (ORF) in human ASP cDNA predicted 313 amino acid long protein that is 92% identical to bovine ASP encoded protein (see FIG. 2). The molecular weight is estimated to be 36 kD. The predicted protein sequence has potentially one "N" glycosylation and 7 phosphorylation sites. The amino acid sequence motifs GGTHGNE (SEQ ID NO: 10), DCTV (SEQ ID NO: 24) and VNEAAYY (SEQ ID NO: 11) identified in both proteins, are similar to the consensus sequences GXXHG/AXE/D (SEQ ID NO: 25), DXXFN (SEQ ID NO: 26) and VXEXXXY (SEQ ID NO: 27) involved in the catalysis by esterasee[19].

Example 9

Tissue Distribution and Size of Aspartoacylase Transcripts

Human poly(A)$^+$ RNA, 2 μg each from various tissues, were analyzed by Northern blot analysis (FIG. 3). The poly (A)$^+$ RNA from human liver gave a single band of 1.44 kb, whereas that from other human tissues tested gave two bands of 1.44 and 5.4 kb. The 1.44 kb faster moving band was similar in size to the 1.435 kbp human ASP cDNA. It appears that human brain expresses a relatively higher proportion of the larger transcript, as compared to relative amounts of the two transcripts in each of the tissues analyzed. The intensity of signals for both bands was highest in human skeletal muscles, followed by kidney and brain.

Example 10

Expression of Aspartoacylase Activity in Human Lung cDNA

The orientation of human ASP cDNA (pHLASP) cloned in pBluescript SK$^-$ phagemid vector is shown in FIG. 4. The cDNA was cloned as an Eco RI and Xho I insert in pBluescript SK$^-$ phagemid in 5'→3' direction. The transcription of human ASP cDNA, driven by LACZ promoter, was studied in the absence and presence of the LACZ inducer isopropylthio-β-D-galactoside (IPTG) in E. coli (XL1 Blue strain). The mean aspartoacylase activity expressed by the pHLASP construct was 0.111, (range 0.044-0.175), mU/mg protein in the absence of IPTG. The activity increased 4-fold to 0.436 (range 0.223-0.622) mU/mg protein when cultures were grown in the presence of 20 mM IPTG. The level of activity expressed by pHLASP was more than 2 orders of magnitude higher than the mean residual activity of 0.019 (range 0.000-0.043) mU/mg protein observed with wild type pBluescript SK$^-$ in the presence of IPTG. These results demonstrate that human ASP cDNA codes for aspartoacylase.

Example 11

Determination of a Missense Mutation in Human ASP cDNA from Patients with CD

The ASP encoded transcripts were analyzed from family members of 17 unrelated pedigrees of Ashkenazi Jewish background. Representative nucleotide sequence data for mutation analysis is shown in FIG. 5. A base change a854>c was identified in patients with CD. Both parents of a854>c homozygous patients were carriers for this mutation. Normal controls and non-carrier sibling of patients with CD did not have the a854>c base change in their ASP encoded transcript. The a854>c base change would alter the E285 codon in aspartoacylase and result in E285>A missense mutation.

The a854>c base change creates recognition sequences for Eag I and Not I restriction endonuclease in the mutant allele. The mutation was analyzed in an amplified 237 bp cDNA fragment for single strand conformation polymorphism (SSCP) and by digestion with restriction endonuclease Eag I. Typical mutation analysis profile from three representative pedigrees are shown in FIG. 6. Individuals homozygous, heterozygous or non-carriers for a854>c mutation could be differentiated by SSCP analysis (see FIG. 6, Panel A). Following digestion of the 237 bp fragment with Eag I (FIG. 6, Panel B), probands homozygous for the a854>c point mutation produced two restriction fragments of 125 and 112 bp; obligate carriers and heterozygotes had an undigested 237 bp fragment and two restriction fragments of 125 and 112 bp, while normal controls and non-carriers for a854>c point mutation had only the 237 bp fragment. The a854>c base mutation was observed in 85% (29 out of 34) of the Canavan alleles and is inherited as a Mendelian recessive trait. Of the 17 probands, 12 were found to be homozygous and 5 were heterozygous for this mutation. In the 5 compound heterozygote patients with CD, the mutation on a second Canavan allele was further investigated. The a854>c base change was not observed in any of 84 normal individuals analyzed so far.

Example 12

Additional Mutations Identified

In addition to the major mutation present in 85% of the Canavan patients and carriers, two other mutations were identified using similar analyses.

One is a c693>a mutation, which results in the codon change TAC>TAA, which results in a translation error of Y231>X; thus, this mutation causes premature termination of the polypeptide chain at the location where a tyrosine residue is supposed to be. This is a "nonsense" mutation.

Another allele which has been identified is a c914>a change, which results in the codon change GCA>GAA, which in turn results in the missense mutation A305>E, substituting a glutamic acid for an alanine residue.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

REFERENCES

1. Globus, J. H. & Strauss, I. Progressive degenerative subcortical encephalopathy (Schilder's disease). *Arch. Neurol. Psychiat.* 20, 1190-1228 (1928).
2. Canavan, M. M. Schilder's encephalitis periaxialis diffusa. *Arch. Neurol. Psychiat.* 25, 299-308 (1931).
3. van Bogaert, L. & Bertrand, I. Sur une idiotie familiale avec degerescence sponglieuse de neuraxe (note preliminaire). *Acta. Neurol. Belg.* 49, 572-587 (1949).
4. Adachi, M., Torii, J., Schneck, L. & Volk, B. W. Electron microscopic and enzyme histochemical studies of the cerebellum in spongy degeneration (van Bogaert and Bertrand type). *Acta. Neuropath.* 20, 22-31 (1972).
5. Adornato, B. T., O'Brien, J. S., Lampert, P. W., Roe, T. F. & Neustein, H. B. Cerebral spongy degeneration of infancy: a biochemical and ultrastructural study of affected twins. *Neurology* 22, 202-210 (1972).
6. Matalon, R., Michals, K., Sebasta, D., Deanching, M., Gashkoff, P. & Casanova, J. Aspartoacylase deficiency and N-acetylaspartic aciduria in patients with Canavan Disease. *Am. J. Med. Genet.* 29, 463-471 (1988).
7. Birnbaum, S. M. Amino acid acylases I and II from hog kidney. *Methods Enzymol.* 2, 115-119 (1955).
8. Birnbaum, S. M., Levinton, L., Kingsley, R. B. & Greenstein, J. P. Specificity of amino acid acylases. *J. Biol. Chem.* 194, 455-462 (1952).
9. Matalon, R., Kaul R., Casanova, J., Michals, K. Johnson A., Rapin, I., Gashkoff, P. & Deanching, M. Aspartoacylase deficiency: the enzyme defect in Canavan Disease. *J. Inher. Met. Dis.* 12, 329-331 (1989).
10. Matalon, R., Kaul, R. & Michals, K. Canavan disease: biochemical and molecular studies. *J. Inher. Metab. Dis.* (in press).
11. Grodd, W., Krägeloh-Mann, I., Petersen, D., Trefz, F. K. & Harzer, K. In vivo asessment of N-acetylaspartate in brain in spongy degeneration (Canavan disease) by proton spectroscopy. *Lancet* 336, 437-438 (1990).
12. Matalon, R., Kaul, R. & Michals, K. In *The Molecular Biology and Genetic Basis of Neurological Disease*, (eds Rosenberg, R. N. et al.) 541-546 (Butterworth-Heineman, Boston, 1993).
13. Ozand, P. T., Gascon, G. & Dhalla, M. Aspartoacylase deficiency and canavan disease in Saudi Arabia. *Am. J. Med. Genet.* 35, 266-268 (1990).
14. Michelakakis, H., Giouroukos, S., Divry, P., Katsarou, E., Rolland, M. O. & Skardoutsow A. Canavan Disease: findings in four new cases. *J. Inher. Matab. Dis.* 14, 267-268 (1991).
15. Matalon, R., Michals, K., Gashkoff, P. & Kaul, R. Prenatal diagnosis of Canavan disease. *J. Inher. Metab. Dis.* 15, 392-394 (1992).
16. Kaul, R., Casanova, J, Johnson, A, Tang, P. & Matalon, R. Purification, characterization and localization of aspartoacylase from bovine brain. *J. Neurochem.* 56, 129-135 (1991).
17. Proudfoot N. J. & Brownlee, G. G. 3' Non-coding region sequences in eukaryotic messenger RNA. *Nature* 263, 211-214 (1976).
18. Birnstiel, M. L., Busslinger, M. & Strub, K. Transcription termination and 3' processing: the end is in site! *Cell* 41, 349-359 (1985).
19. Cygler, M. et al. Relationship between sequence conservation and three-dimensional structure in a large family of esterases, lipases, and related proteins. *Protein Science* 2, 366-382 (1993).
20. Lemeur, M. A., Galliot, B. & Gerlinger, P. Termination of the ovalbumin gene transcription. *EMBO J.* 3, 2779-2786 (1984).
21. Miller, Y. R., Drabkin, H., Jones, C. & Fisher, J. H. Human aminoacylase-1: cloning, regional assignment to distal chromosome 3p21.1, and identification of a cross-hybridizing sequence on chromosome 18. *Genomics* 8, 149-154 (1990).
22. Goldstein, F. B. Biosynthesis of N-acetyl-L-aspartic acid. *J. Biol. Chem.* 234, 2702-2706 (1959).
23. Goldstein, F. B. The enzymatic synthesis of N-acetyl-L-aspartic acid by subcellular preparations of rat brain. *J. Biol. Chem.* 244, 4257-4260 (1969).
24. Moffett, J. R., Namboodiri, M. A., Cangro, C. B. & Neale, J. H. Immunohistochemical localization of N-acetylaspartate in rat brain. *NeuroReport* 2, 131-134 (1991).

25. Urenjak, J., Williams, S. R., Gadian, D. G. & Noble, M. Specific expression of N-acetylaspartate in neurons, oligodendrocyte-type-2 astrocyte progenitors, and immature oligodendrocytes in vitro. *J. Neurochem.* 59, 55-61 (1992).
26. Moffett, J. R., Namboodiri, M. A. & Neale, J. H. Enhanced carbodiimide fixation for immunohistochemistry: application to the comparative distributions of N-acetylaspartylglutamate and N-acetylaspartate immunoreactivities in rat brain. *J. Histochem. Cytochem.* 31, 559-570 (1993).
27. Tallan, H. H., Moore, S. & Stein, W. H. N-Acetyl-L-aspartic acid in brain. *J. Biol. Chem.* 219, 257-264 (1956).
28. Jacobson, K. B. Studies on the role of N-acetylaspartic acid on mammalian brain. *J. Gen. Physiol.* 43, 323-333 (1957).
29. McIntosh, J. M. & Cooper, J. R. Studies on the function of N-acetylaspartic acid in the brain. *J. Neurochem.* 12, 825-835 (1965).
30. Shigematsu, H. et al. Purification and characterization of the heat stable factors essential for conversion of lignoceric acid to cerebronic acid and glutamic acid: identification of N-acetyl-L-aspartic acid. *J. Neurochem.* 40, 814-820 (1983).
31. Cangro, C. B., Namboodiri, M. A. A., Sklae, L. A., Corigliano-Murphy, A. & Neale, J. H. Immunocytochemistry and biosynthesis of N-acetylaspartylglutamate in spinal sensory ganglia. *J. Neurochem.* 49, 1579-1588 (1987).
32. Ory-Lavollee, L., Blakely R. D. & Coyle, J. T. Neurochemical and immunocytochemical studies on the distribution of N-acetylaspartylglutamate and N-acetyl-aspartate in rat spinal cord and some peripheral nervous tissues. *J. Neurochem.* 48, 895-899 (1987).
33. Birken, D. L. & Oldendorf, W. H. N-Acetyl-L-aspartic acid: A literature review of a compound prominent in $^1$H-NMR spectroscopic studies on brain. *Neurosci. Behavioral Rev.* 13, 23-31 (1989).
34. Grood, W., Krägeloh-Mann, I., Klose, U. & Sauter, R. Metabolic and destructive brain disorders in children: Finding with localized proton MR spectroscopy. *Radiology* 181, 173-181 (1991).
35. Dunlop, D. S, McHale, D. M. & Lajtha, A. Decreased brain N-acetylaspartate in Huntington's disease. *Brain Research* 580, 44-48 (1992).
36. Meyerhoff, D. J. et al. Reduced brain N-acetylaspartate suggests neuronal loss in cognitively impaired human immunodeficiency virus-seropositive individuals: In vivo $^1$H magnetic resonance spectroscopic imaging. *Neurology* 43, 509-515 (1993).
37. Gideon, P. et al. Early time course of N-acetylspartate, creatine and phosphocreatine, and compounds containing choline in the brain after acute stroke-a proton magnetic resonance spectroscopy study. *Stroke* 23, 1566-1572 (1992).
38. Marcucci, F., Colombo, L., De Ponte, G. & Mussini, E. Decrease in N-acetyl-L-aspartic acid in brain of myodystrophic mice. *J. Neurochem.* 43, 1484-1486 (1984).
39. Bell, J. D. et al. In vivo detection of metabolic changes in a mouse model of scrapie using nuclear magnetic resonance spectroscopy. *J. Gen. Virology* 72, 2419-2423 (1991)
40. Kaul, R., Murthy S. N. P., Reddy A. G., Steck, T. L. & Kohler, H. Amino acid sequence of the N-terminal 201 residues of human erythrocyte membrane band 3. *J. Biol. Chem.* 258, 7981-7990 (1983).
41. Saiki, R. K. et al. Enzymatic amplification of β-globin genomic sequences and restriction site analysis for diagnosis of sickle cell anemia. *Science* 230, 1350-1354 (1985).
42. Orita, M., Suzuki, Y., Sekiya, T. & Hayashi, K. Rapid and sensitive detection of point mutations and DNA polymorphisms using the polymerase chain reaction. *Genomics* 5, 874-879 (1989).
43. Feinberg, A. P. & Vogelstein, B. Technique for radio labelling DNA restriction endonuclease fragments to high specific activity. *Anal. Biochem.* 137, 266-267 (1984).
44. Kaul, R., Hidebrand, B. Roberts, S. & Jagadeeswaran, P. Isolation and characterization of human blood coagulation factor X cDNA. *Gene* 41, 311-314 (1986).
45. Sambrook, J., Fritsch, E. F. & Maniatis, T. *Molecular Cloning: A laboratory manual,* 2nd ed. (Cold Spring Harbour Laboratory, New York, 1989).
46. Sanger, F. S., Nicklen, I. & Coulson, A. R. DNA sequencing with chain terminating inhibitors. *Proc. Natl. Acad. Sci. U.S.A.* 74, 5463-5467 (1977).
47. Chomczynski, P. & Sacchi, N. Single step method of RNA isolation by acid guanidinium thiocyanate-phenol-chloroform extraction. *Anal. Biochem.* 162, 156 (1987).
48. Lowry, O. H., Rosenbroug, N. J., Farr, A. L. & Randall, R. J. Protein measurement with the folin phenol reagent. *J. Biol. Chem.* 193, 265-275 (1951).
49. Kohler and Millstein, *Nature* 256, 495 (1975).
50. *Human Gene Therapy,* 1(#1)-4(#4) et seq., (1990-1993), W. French Anderson, M. D., ed., Mary Ann Leibert, Inc., New York City, N.Y.
51. Erickson, *Am. J. Hum. Genet.* 43, 582 (1988).

What is claimed is:

1. A kit for assaying for the presence of a human aspartoacylase gene by immunoassay, comprising:
   (a) an antibody which specifically binds to a gene product of the human aspartoacylase gene;
   (b) a reagent means for detecting binding of the antibody to the gene product; wherein the antibody and reagent means are each present in amounts effective to perform the immunoassay.

2. The kit of claim 1, wherein said reagent means for detecting binding comprises fluorescence detection, radioactive decay detection, enzyme activity detection or colorimetric detection.

3. The kit of claim 2, wherein said aspartocylase gene is wild-type human aspartoacylase gene.

4. The kit of claim 2, wherein said aspartoacylase gene is a mutant human aspartoacylase gene.

5. The kit of claim 1 wherein said antibody is a monoclonal antibody that is specific for said gene product of human aspartoacylase gene.

6. The kit of claim 1, wherein said antibody molecule comprises an F'(ab)$_2$ fragment which binds to said gene product of human aspartoacylase gene.

7. An immunologically active anti-aspartoacylase antibody which is specific for a human aspartoacylase polypeptide, wherein said aspartoacylase poplypeptide is capable of hydrolyzing N-acetyl-aspartic acid to aspartate and acetate.

8. The antibody of claim 7, which is a monoclonal antibody that is specific for said wild type aspartoacylase.

9. The antibody of claim 7, wherein said antibody molecule comprises an F'(ab)$_2$ fragment which binds to said wild type aspartoacylase.

10. An immunologically active anti-aspartoacylase antibody which is specific for a mutant aspartoacylase polypeptide having either an altered ability to hydrolyze N-acetyl-aspartic acid to aspartate and acetate, as compared with a wild-type human aspartoacylase, or incapable of hydrolyzing N-acetyl-aspartic acid to aspartate and acetate, and comprising the polypeptide sequence set forth in SEQ ID NO: 2 or a wild-type human aspartoacylase, except that said sequence has one or more of the following amino acid substitutions: E285>A, Y231>X, and/or A305>E, whereby E is glutamate, A is alanine, Y is tyrosine, and X is any naturally-occurring amino acid.

11. The antibody of claim 10, which is a monoclonal antibody that is specific for said mutant aspartoacylase.

12. The antibody of claim 10, wherein said antibody molecule comprises an F'(ab)₂ fragment which binds to said mutant aspartoacylase.

13. A hybridoma which produces a monoclonal antibody of claim 8, wherein said antibody is specific for a wild-type aspartoacylase polypeptide.

14. The hybridoma of claim 13 wherein said antibody is specific for said wild-type human aspartoacylase polypeptide.

15. A hybridoma which produces a monoclonal antibody of claim 11, wherein said antibody is specific for a mutant aspartoacylase polypeptide.

16. The hybridoma of claim 15 wherein said antibody is specific for said mutant aspartoacylase polypeptide having either an altered ability to hydrolyze N-acetyl-aspartic acid to aspartate and acetate, as compared with a wild-type human aspartoacylase, or incapable of hydrolyzing N-acetyl-aspartic acid to aspartate and acetate, and comprising the polypeptide sequence set forth in SEQ ID NO: 2 or wild-type human aspartoacylase, except that said sequence has one or more of the following amino acid substitutions: E285>A, Y231>X, and/or A305>E, wherein E is glutamate, A is alanine, Y is tyrosine, and X is any naturally-occurring amino acid.

17. An antibody which is specific for human aspartoacylase polypeptide, wherein said polypeptide comprises the sequence set forth in SEQ ID NO: 2 or a variant of SEQ ID NO: 2 having at least one amino acid substitution which is E285>A, Y231>X, and/or A305>E, whereby E is glutamate, A is alanine, Y is tyrosine, and X is any naturally-occurring amino acid.

* * * * *

```
                         SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
       (A) LENGTH: 1435 base pairs
       (B) TYPE: nucleic acid
       (C) STRANDEDNESS: double
       (D) TOPOLOGY: linear (ix) FEATURE:
       (A) NAME/KEY: CDS
       (B) LOCATION: 159..1097
```

(xi) SEQUENCE DESCRIPTION: SEQ ID NO: 1:

```
TTGTAACAGA AAATTAAAAT ATACTCCACT CAAGGGAATT CTGTACTTTG CCCTTTTGGT      60

AAAGTCTCAT TTACATTTCT AAACCTTTCT TAAGAAAATC GAATTTCCTT TGATCTCTCT     120

TCTGAATTGC AGAAATCAGA TAAAAACTAC TTGGTGAA ATG ACT TCT TGT CAC          173
                                       Met Thr Ser Cys His
                                        1               5

ATT GCT GAA GAA CAT ATA CAA AAG GTT GCT ATC TTT GGA GGA ACC CAT        221
Ile Ala Glu Glu His Ile Gln Lys Val Ala Ile Phe Gly Gly Thr His
             10                  15                  20

GGG AAT GAG CTA ACC GGA GTA TTT CTG GTT AAG CAT TGG CTA GAG AAT        269
Gly Asn Glu Leu Thr Gly Val Phe Leu Val Lys His Trp Leu Glu Asn
         25                  30                  35

GGC GCT GAG ATT CAG AGA ACA GGG CTG GAG GTA AAA CCA TTT ATT ACT        317
Gly Ala Glu Ile Gln Arg Thr Gly Leu Glu Val Lys Pro Phe Ile Thr
     40                  45                  50

AAC CCC AGA GCA GTG AAG AAG TGT ACC AGA TAT ATT GAC TGT GAC CTG        365
Asn Pro Arg Ala Val Lys Lys Cys Thr Arg Tyr Ile Asp Cys Asp Leu
 55                  60                  65

AAT CGC ATT TTT GAC CTT GAA AAT CTT GGC AAA AAA ATG TCA GAA GAT        413
Asn Arg Ile Phe Asp Leu Glu Asn Leu Gly Lys Lys Met Ser Glu Asp
 70                  75                  80                  85

TTG CCA TAT GAA GTG AGA AGG GCT CAA GAA ATA AAT CAT TTA TTT GGT        461
Leu Pro Tyr Glu Val Arg Arg Ala Gln Glu Ile Asn His Leu Phe Gly
                 90                  95                 100

CCA AAA GAC AGT GAA GAT TCC TAT GAC ATT ATT TTT GAC CTT CAC AAC        509
Pro Lys Asp Ser Glu Asp Ser Tyr Asp Ile Ile Phe Asp Leu His Asn
            105                 110                 115

ACC ACC TCT AAC ATG GGG TGC ACT CTT ATT CTT GAG GAT TCC AGG AAT        557
Thr Thr Ser Asn Met Gly Cys Thr Leu Ile Leu Glu Asp Ser Arg Asn
        120                 125                 130

AAC TTT TTA ATT CAG ATG TTT CAT TAC ATT AAG ACT TCT CTG GCT CCA        605
Asn Phe Leu Ile Gln Met Phe His Tyr Ile Lys Thr Ser Leu Ala Pro
    135                 140                 145

CTA CCC TGC TAC GTT TAT CTG ATT GAG CAT CCT TCC CTC AAA TAT GCG        653
Leu Pro Cys Tyr Val Tyr Leu Ile Glu His Pro Ser Leu Lys Tyr Ala
150                 155                 160                 165

ACC ACT CGT TCC ATA GCC AAG TAT CCT GTG GGT ATA GAA GTT GGT CCT        701
Thr Thr Arg Ser Ile Ala Lys Tyr Pro Val Gly Ile Glu Val Gly Pro
                170                 175                 180

CAG CCT CAA GGG GTT CTG AGA GCT GAT ATC TTG GAT CAA ATG AGA AAA        749
Gln Pro Gln Gly Val Leu Arg Ala Asp Ile Leu Asp Gln Met Arg Lys
            185                 190                 195

ATG ATT AAA CAT GCT CTT GAT TTT ATA CAT CAT TTC AAT GAA GGA AAA        797
Met Ile Lys His Ala Leu Asp Phe Ile His His Phe Asn Glu Gly Lys
        200                 205                 210

GAA TTT CCT CCC TGC GCC ATT GAG GTC TAT AAA ATT ATA GAG AAA GTT        845
Glu Phe Pro Pro Cys Ala Ile Glu Val Tyr Lys Ile Ile Glu Lys Val
    215                 220                 225

GAT TAC CCC CGG GAT GAA AAT GGA GAA ATT GCT GCT ATC ATC CAT CCT        893
Asp Tyr Pro Arg Asp Glu Asn Gly Glu Ile Ala Ala Ile Ile His Pro
230                 235                 240                 245

AAT CTG CAG GAT CAA GAC TGG AAA CCA CTG CAT CCT GGG GAT CCC ATG        941
Asn Leu Gln Asp Gln Asp Trp Lys Pro Leu His Pro Gly Asp Pro Met
                250                 255                 260

TTT TTA ACT CTT GAT GGG AAG ACG ATC CCA CTG GGC GGA GAC TGT ACC        989
Phe Leu Thr Leu Asp Gly Lys Thr Ile Pro Leu Gly Gly Asp Cys Thr
            265                 270                 275

GTG TAC CCC GTG TTT GTG AAT GAG GCC GCA TAT TAC GAA AAG AAA GAA       1037
```

```
Val Tyr Pro Val Phe Val Asn Glu Ala Ala Tyr Tyr Glu Lys Lys Glu
        280                 285                 290

GCT TTT GCA AAG ACA ACT AAA CTA ACG CTC AAT GCA AAA AGT ATT CGC    1085
Ala Phe Ala Lys Thr Thr Lys Leu Thr Leu Asn Ala Lys Ser Ile Arg
        295                 300                 305

TGC TGT TTA CAT TAGAAATCAC TTCCAGCTTA CATCTTACAC GGTGTCTTAC        1137
Cys Cys Leu His
310

AAATTCTGCT AGTCTGTAAG CTCCTTAAGA GTAGGGTTGT GCCTTATTCA ACTGCATACA  1197

TAGCTCCTAG CACAGTGCCT TATTCGGTAG GCATCTAAGC AAATTTCTTA AATTAATTAA  1257

TATATCTTTA AAGATATCAT ATTTTATGTA TGTAGCTTAT TCAAGAAGT GTTTCCTATT   1317

TCTATATAGT TTATTATACA TGATACTTGG GTAGCTCAAC ATTCTTAATA AACAGCCTTT  1377

GTATTCAGAA TATAAAATTG AAATAGATAT ATATAAAGTT AAAAAAAAAA AAAAAAA     1435
```

(2) INFORMATION FOR SEQ ID NO: 2:

(i) SEQUENCE CHARACTERISTICS:
        (A) LENGTH: 313 amino acids
        (B) TYPE: amino acid
        (D) TOPOLOGY: linear (ix) FEATURE:
        (A) NAME/KEY: Modified-site
        (B) LOCATION: 83
        (D) OTHER INFORMATION: /note= "Phosphorylation site"

(ix) FEATURE:
        (A) NAME/KEY: Modified-site
        (B) LOCATION: 105
        (D) OTHER INFORMATION: /note= "Phosphorylation site"

(ix) FEATURE:
        (A) NAME/KEY: Modified-site
        (B) LOCATION: 108
        (D) OTHER INFORMATION: /note= "Phosphorylation site"

(ix) FEATURE:
        (A) NAME/KEY: Modified-site
        (B) LOCATION: 146
        (D) OTHER INFORMATION: /note= "Phosphorylation site"

(ix) FEATURE:
        (A) NAME/KEY: Modified-site
        (B) LOCATION: 264
        (D) OTHER INFORMATION: /note= "Phosphorylation site"

(ix) FEATURE:
        (A) NAME/KEY: Modified-site
        (B) LOCATION: 117
        (D) OTHER INFORMATION: /note= "Potential N-glycosylation
           site"

(ix) FEATURE:
        (A) NAME/KEY: Active-site
        (B) LOCATION: 18..24
        (D) OTHER INFORMATION: /note= "Consensus sequence
           predicted to be involved in catalysis"

(ix) FEATURE:
        (A) NAME/KEY: Active-site
        (B) LOCATION: 275..278
        (D) OTHER INFORMATION: /note= "Consensus sequence
           predicted to be involved in catalysis"

(ix) FEATURE:
        (A) NAME/KEY: Active-site
        (B) LOCATION: 283..289
        (D) OTHER INFORMATION: /note= "Consensus sequence
           predicted to be involved in catalysis"

(xi) SEQUENCE DESCRIPTION: SEQ ID NO: 2:

-continued

```
Met Thr Ser Cys His Ile Ala Glu Glu His Ile Gln Lys Val Ala Ile
1               5                   10                  15

Phe Gly Gly Thr His Gly Asn Glu Leu Thr Gly Val Phe Leu Val Lys
                20                  25                  30

His Trp Leu Glu Asn Gly Ala Glu Ile Gln Arg Thr Gly Leu Glu Val
                35                  40                  45

Lys Pro Phe Ile Thr Asn Pro Arg Ala Val Lys Lys Cys Thr Arg Tyr
50                  55                  60

Ile Asp Cys Asp Leu Asn Arg Ile Phe Asp Leu Glu Asn Leu Gly Lys
65                  70                  75                  80

Lys Met Ser Glu Asp Leu Pro Tyr Glu Val Arg Arg Ala Gln Glu Ile
                85                  90                  95

Asn His Leu Phe Gly Pro Lys Asp Ser Glu Asp Ser Tyr Asp Ile Ile
                100                 105                 110

Phe Asp Leu His Asn Thr Thr Ser Asn Met Gly Cys Thr Leu Ile Leu
                115                 120                 125

Glu Asp Ser Arg Asn Asn Phe Leu Ile Gln Met Phe His Tyr Ile Lys
                130                 135                 140

Thr Ser Leu Ala Pro Leu Pro Cys Tyr Val Tyr Leu Ile Glu His Pro
145                 150                 155                 160

Ser Leu Lys Tyr Ala Thr Thr Arg Ser Ile Ala Lys Tyr Pro Val Gly
                165                 170                 175

Ile Glu Val Gly Pro Gln Pro Gln Gly Val Leu Arg Ala Asp Ile Leu
                180                 185                 190

Asp Gln Met Arg Lys Met Ile Lys His Ala Leu Asp Phe Ile His His
                195                 200                 205

Phe Asn Glu Gly Lys Glu Phe Pro Pro Cys Ala Ile Glu Val Tyr Lys
210                 215                 220

Ile Ile Glu Lys Val Asp Tyr Pro Arg Asp Glu Asn Gly Glu Ile Ala
225                 230                 235                 240

Ala Ile Ile His Pro Asn Leu Gln Asp Gln Asp Trp Lys Pro Leu His
                245                 250                 255

Pro Gly Asp Pro Met Phe Leu Thr Leu Asp Gly Lys Thr Ile Pro Leu
                260                 265                 270

Gly Gly Asp Cys Thr Val Tyr Pro Val Phe Val Asn Glu Ala Ala Tyr
                275                 280                 285

Tyr Glu Lys Lys Glu Ala Phe Ala Lys Thr Thr Lys Leu Thr Leu Asn
290                 295                 300

Ala Lys Ser Ile Arg Cys Cys Leu His
305                 310
```

(2) INFORMATION FOR SEQ ID NO: 3:

(i) SEQUENCE CHARACTERISTICS:
        (A) LENGTH: 313 amino acids
        (B) TYPE: amino acid
        (D) TOPOLOGY: linear (ix) FEATURE:
        (A) NAME/KEY: Region
        (B) LOCATION: 6
        (D) OTHER INFORMATION: /note= "This is isoleucine in
           human, valine in bovine. This is a very
           conservative substitution."

(ix) FEATURE:
        (A) NAME/KEY: Region
        (B) LOCATION: 9
        (D) OTHER INFORMATION: /note= "This is glutamic acid in
           human, aspartic acid in bovine. This is a very -continued

```
            conservative substitution."
(ix) FEATURE:
     (A) NAME/KEY: Region
     (B) LOCATION: 10
     (D) OTHER INFORMATION: /note= "This is histidine in human,
         proline in bovine. This is a conservative
         substitution."

(ix) FEATURE:
     (A) NAME/KEY: Region
     (B) LOCATION: 12
     (D) OTHER INFORMATION: /note= "This is glutamine in human,
         lysine in bovine. This is a very conservative
         substitution."

(ix) FEATURE:
     (A) NAME/KEY: Region
     (B) LOCATION: 38
     (D) OTHER INFORMATION: /note= "This is glycine in human,
         serine in bovine. This is a very conservative
         substitution."

(ix) FEATURE:
     (A) NAME/KEY: Region
     (B) LOCATION: 39
     (D) OTHER INFORMATION: /note= "This is alanine in human,
         threonine in bovine. This is a very conservative
         substitution."

(ix) FEATURE:
     (A) NAME/KEY: Region
     (B) LOCATION: 72
     (D) OTHER INFORMATION: /note= "This is isoleucine in
         human, valine in bovine. This is a very
         conservative substitution."

(ix) FEATURE:
     (A) NAME/KEY: Region
     (B) LOCATION: 75
     (D) OTHER INFORMATION: /note= "This is leucine in human,
         proline in bovine. This is not a conservative
         substitution."

(ix) FEATURE:
     (A) NAME/KEY: Region
     (B) LOCATION: 82
     (D) OTHER INFORMATION: /note= "This is methionine in
         human, lysine in bovine. This is a conservative
         substitution."

(ix) FEATURE:
     (A) NAME/KEY: Region
     (B) LOCATION: 134
     (D) OTHER INFORMATION: /note= "This is asparagine in
         human, aspartic acid in bovine. This is a very
         conservative substitution."

(ix) FEATURE:
     (A) NAME/KEY: Region
     (B) LOCATION: 200
     (D) OTHER INFORMATION: /note= "This is lysine in human,
         glutamine in bovine. This is a very conservative
         substitution."

(ix) FEATURE:
     (A) NAME/KEY: Region
     (B) LOCATION: 208
     (D) OTHER INFORMATION: /note= "This is histidine in human,
         asparagine in bovine. This is a very conservative
         substitution."

(ix) FEATURE:
     (A) NAME/KEY: Region
     (B) LOCATION: 226
     (D) OTHER INFORMATION: /note= "This is isoleucine in
         human, methionine in bovine. This is a very
         conservative substitution."

(ix) FEATURE:
```

-continued

```
        (A) NAME/KEY: Region
        (B) LOCATION: 227
        (D) OTHER INFORMATION: /note= "This is glutamic acid in
            human, arginine in bovine.  This is not a
            conservative substitution."

(ix) FEATURE:
        (A) NAME/KEY: Region
        (B) LOCATION: 234
        (D) OTHER INFORMATION: /note= "This is aspartic acid in
            human, asparagine in bovine.  This is a very
            conservative substitution."

(ix) FEATURE:
        (A) NAME/KEY: Region
        (B) LOCATION: 236
        (D) OTHER INFORMATION: /note= "This is asparagine in
            human, serine in bovine.  This is a very
            conservative substitution."

(ix) FEATURE:
        (A) NAME/KEY: Region
        (B) LOCATION: 240
        (D) OTHER INFORMATION: /note= "This is alanine in human,
            serine in bovine.  This is a very conservative
            substitution."

(ix) FEATURE:
        (A) NAME/KEY: Region
        (B) LOCATION: 246
        (D) OTHER INFORMATION: /note= "This is asparagine in
            human, lysine in bovine.  This is a very
            conservative substitution."

(ix) FEATURE:
        (A) NAME/KEY: Region
        (B) LOCATION: 258
        (D) OTHER INFORMATION: /note= "This is glycine in human,
            glutamic acid in bovine.  This is a conservative
            substitution."

(ix) FEATURE:
        (A) NAME/KEY: Region
        (B) LOCATION: 261
        (D) OTHER INFORMATION: /note= "This is methionine in
            human, valine in bovine.  This is a very
            conservative substitution."

(ix) FEATURE:
        (A) NAME/KEY: Region
        (B) LOCATION: 276
        (D) OTHER INFORMATION: /note= "This is cysteine in human,
            glutamine in bovine.  This is not a conservative
            substitution."

(ix) FEATURE:
        (A) NAME/KEY: Region
        (B) LOCATION: 306
        (D) OTHER INFORMATION: /note= "This is lysine in human,
            asparagine in bovine.  This is a very conservative
            substitution."

(ix) FEATURE:
        (A) NAME/KEY: Region
        (B) LOCATION: 310
        (D) OTHER INFORMATION: /note= "This is cysteine in human,
            serine in bovine.  This is a conservative substitution."

(ix) FEATURE:
        (A) NAME/KEY: Region
        (B) LOCATION: 311
        (D) OTHER INFORMATION: /note= "This is cysteine in human,
            serine in bovine.  This is a conservative substitution."

(ix) FEATURE:
        (A) NAME/KEY: Modified-site
        (B) LOCATION: 83
        (D) OTHER INFORMATION: /note= "Phosphorylation site"

(ix) FEATURE:
```

(A) NAME/KEY: Modified-site
        (B) LOCATION: 105
        (D) OTHER INFORMATION: /note= "Phosphorylation site"

(ix) FEATURE:
        (A) NAME/KEY: Modified-site
        (B) LOCATION: 108
        (D) OTHER INFORMATION: /note= "Phosphorylation site"

(ix) FEATURE:
        (A) NAME/KEY: Modified-site
        (B) LOCATION: 146
        (D) OTHER INFORMATION: /note= "Phosphorylation site"

(ix) FEATURE:
        (A) NAME/KEY: Modified-site
        (B) LOCATION: 264
        (D) OTHER INFORMATION: /note= "Phosphorylation site"

(ix) FEATURE:
        (A) NAME/KEY: Modified-site
        (B) LOCATION: 117
        (D) OTHER INFORMATION: /note= "Potential N-glycosylation site"

(ix) FEATURE:
        (A) NAME/KEY: Active-site
        (B) LOCATION: 18..24
        (D) OTHER INFORMATION: /note= "Consensus sequence
            predicted to be involved in catalysis"

(ix) FEATURE:
        (A) NAME/KEY: Active-site
        (B) LOCATION: 275..278
        (D) OTHER INFORMATION: /note= "Consensus sequence
            predicted to be involved in catalysis"

(ix) FEATURE:
        (A) NAME/KEY: Active-site
        (B) LOCATION: 283..289
        (D) OTHER INFORMATION: /note= "Consensus sequence
            predicted to be involved in catalysis"

(xi) SEQUENCE DESCRIPTION: SEQ ID NO: 3:

```
Met Thr Ser Cys His Xaa Ala Glu Xaa Xaa Ile Xaa Lys Val Ala Ile
1               5                   10                  15

Phe Gly Gly Thr His Gly Asn Glu Leu Thr Gly Val Phe Leu Val Lys
            20                  25                  30

His Trp Leu Glu Asn Xaa Xaa Glu Ile Gln Arg Thr Gly Leu Glu Val
        35                  40                  45

Lys Pro Phe Ile Thr Asn Pro Arg Ala Val Lys Lys Cys Thr Arg Tyr
    50                  55                  60

Ile Asp Cys Asp Leu Asn Arg Xaa Phe Asp Xaa Glu Asn Leu Gly Lys
65                  70                  75                  80

Lys Xaa Ser Glu Asp Leu Pro Tyr Glu Val Arg Arg Ala Gln Glu Ile
            85                  90                  95

Asn His Leu Phe Gly Pro Lys Asp Ser Glu Asp Ser Tyr Asp Ile Ile
            100                 105                 110

Phe Asp Leu His Asn Thr Thr Ser Asn Met Gly Cys Thr Leu Ile Leu
            115                 120                 125

Glu Asp Ser Arg Asn Xaa Phe Leu Ile Gln Met Phe His Tyr Ile Lys
130                 135                 140

Thr Ser Leu Ala Pro Leu Pro Cys Tyr Val Tyr Leu Ile Glu His Pro
145                 150                 155                 160

Ser Leu Lys Tyr Ala Thr Thr Arg Ser Ile Ala Lys Tyr Pro Val Gly
            165                 170                 175

Ile Glu Val Gly Pro Gln Pro Gln Gly Val Leu Arg Ala Asp Ile Leu
            180                 185                 190
```

```
Asp Gln Met Arg Lys Met Ile Xaa His Ala Leu Asp Phe Ile His Xaa
            195                 200                 205

Phe Asn Glu Gly Lys Glu Phe Pro Pro Cys Ala Ile Glu Val Tyr Lys
    210                 215                 220

Ile Xaa Xaa Lys Val Asp Tyr Pro Arg Xaa Glu Xaa Gly Glu Ile Xaa
225                 230                 235                 240

Ala Ile Ile His Pro Xaa Leu Gln Asp Gln Asp Trp Lys Pro Leu His
                245                 250                 255

Pro Xaa Asp Pro Xaa Phe Leu Thr Leu Asp Gly Lys Thr Ile Pro Leu
        260                 265                 270

Gly Gly Asp Xaa Thr Val Tyr Pro Val Phe Val Asn Glu Ala Ala Tyr
            275                 280                 285

Tyr Glu Lys Lys Glu Ala Phe Ala Lys Thr Thr Lys Leu Thr Leu Asn
    290                 295                 300

Ala Xaa Ser Ile Arg Xaa Xaa Leu His
305                 310
```

(2) INFORMATION FOR SEQ ID NO: 4:

(i) SEQUENCE CHARACTERISTICS:
        (A) LENGTH: 313 amino acids
        (B) TYPE: amino acid
        (D) TOPOLOGY: linear (ix) FEATURE:
        (A) NAME/KEY: Modified-site
        (B) LOCATION: 83
        (D) OTHER INFORMATION: /note= "Phophorylation site"

(ix) FEATURE:
        (A) NAME/KEY: Modified-site
        (B) LOCATION: 105
        (D) OTHER INFORMATION: /note= "Phosphorylation site"

(ix) FEATURE:
        (A) NAME/KEY: Modified-site
        (B) LOCATION: 108
        (D) OTHER INFORMATION: /note= "Phosphorylation site"

(ix) FEATURE:
        (A) NAME/KEY: Modified-site
        (B) LOCATION: 146
        (D) OTHER INFORMATION: /note= "Phosphorylation site"

(ix) FEATURE:
        (A) NAME/KEY: Modified-site
        (B) LOCATION: 264
        (D) OTHER INFORMATION: /note= "Phosphorylation site"

(ix) FEATURE:
        (A) NAME/KEY: Modified-site
        (B) LOCATION: 117
        (D) OTHER INFORMATION: /note= "Potential N-glycosylation
            site"

(ix) FEATURE:
        (A) NAME/KEY: Active-site
        (B) LOCATION: 18..24
        (D) OTHER INFORMATION: /note= "Consensus sequence
            predicted to be involved in catalysis"

(ix) FEATURE:
        (A) NAME/KEY: Active-site
        (B) LOCATION: 275..278
        (D) OTHER INFORMATION: /note= "Consensus sequence
            predicted to be involved in catalysis"

(ix) FEATURE:
        (A) NAME/KEY: Active-site
        (B) LOCATION: 283..289
        (D) OTHER INFORMATION: /note= "Consensus sequence
            predicted to be involved in catalysis"

-continued (xi) SEQUENCE DESCRIPTION: SEQ ID NO: 4:

```
Met Thr Ser Cys His Val Ala Glu Asp Pro Ile Lys Lys Val Ala Ile
1               5                   10                  15

Phe Gly Gly Thr His Gly Asn Glu Leu Thr Gly Val Phe Leu Val Lys
            20                  25                  30

His Trp Leu Glu Asn Ser Thr Glu Ile Gln Arg Thr Gly Leu Glu Val
        35                  40                  45

Lys Pro Phe Ile Thr Asn Pro Arg Ala Val Lys Lys Cys Thr Arg Tyr
    50                  55                  60

Ile Asp Cys Asp Leu Asn Arg Val Phe Asp Pro Glu Asn Leu Gly Lys
65                  70                  75                  80

Lys Lys Ser Glu Asp Leu Pro Tyr Glu Val Arg Arg Ala Gln Glu Ile
                85                  90                  95

Asn His Leu Phe Gly Pro Lys Asp Ser Glu Asp Ser Tyr Asp Ile Ile
            100                 105                 110

Phe Asp Leu His Asn Thr Thr Ser Asn Met Gly Cys Thr Leu Ile Leu
        115                 120                 125

Glu Asp Ser Arg Asn Asp Phe Leu Ile Gln Met Phe His Tyr Ile Lys
130                 135                 140

Thr Ser Leu Ala Pro Leu Pro Cys Tyr Val Tyr Leu Ile Glu His Pro
145                 150                 155                 160

Ser Leu Lys Tyr Ala Thr Thr Arg Ser Ile Ala Lys Tyr Pro Val Gly
                165                 170                 175

Ile Glu Val Gly Pro Gln Pro Gln Gly Val Leu Arg Ala Asp Ile Leu
            180                 185                 190

Asp Gln Met Arg Lys Met Ile Gln His Ala Leu Asp Phe Ile His Asn
        195                 200                 205

Phe Asn Glu Gly Lys Glu Phe Pro Pro Cys Ala Ile Glu Val Tyr Lys
    210                 215                 220

Ile Met Arg Lys Val Asp Tyr Pro Arg Asn Glu Ser Gly Glu Ile Ser
225                 230                 235                 240

Ala Ile Ile His Pro Lys Leu Gln Asp Gln Asp Trp Lys Pro Leu His
                245                 250                 255

Pro Glu Asp Pro Val Phe Leu Thr Leu Asp Gly Lys Thr Ile Pro Leu
            260                 265                 270

Gly Gly Asp Gln Thr Val Tyr Pro Val Phe Val Asn Glu Ala Ala Tyr
        275                 280                 285

Tyr Glu Lys Lys Glu Ala Phe Ala Lys Thr Thr Lys Leu Thr Leu Asn
    290                 295                 300

Ala Asn Ser Ile Arg Ser Ser Leu His
305                 310
```

(2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 5:

AACCCTACTC TTAAGGAC                                            18

(2) INFORMATION FOR SEQ ID NO: 6:

(i) SEQUENCE CHARACTERISTICS:

```
        (A) LENGTH: 19 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 1
        (D) OTHER INFORMATION: /mod_base= OTHER
            /note= "The M13 universal primer tag is attached
            to base number 1."

(xi) SEQUENCE DESCRIPTION: SEQ ID NO: 6:

CCGGGATGAA AATGGAGAA                                              19

(2) INFORMATION FOR SEQ ID NO: 7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 1
        (D) OTHER INFORMATION: /mod_base= OTHER
            /note= "The M13 reverse primer tag is attached to
            base 1."

(xi) SEQUENCE DESCRIPTION: SEQ ID NO: 7:

ACCGTGTAAG ATGTAAGC                                               18

(2) INFORMATION FOR SEQ ID NO: 8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 8:

AGGATCAAGA CTGGAAACC                                              19

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 9:

GTAAGACACC GTGTAAGATG                                             20

(2) INFORMATION FOR SEQ ID NO: 10:

(i) SEQUENCE CHARACTERISTICS:
        (A) LENGTH: 7 amino acids
        (B) TYPE: amino acid
        (D) TOPOLOGY: linear (iii) HYPOTHETICAL: NO (v) FRAGMENT TYPE: internal (xi) SEQUENCE DESCRIPTION: SEQ ID NO: 10:

Gly Gly Thr His Gly Asn Glu
1               5
```

(2) INFORMATION FOR SEQ ID NO: 11:

(i) SEQUENCE CHARACTERISTICS:
        (A) LENGTH: 7 amino acids
        (B) TYPE: amino acid
        (D) TOPOLOGY: linear (iii) HYPOTHETICAL: NO (v) FRAGMENT TYPE: internal (xi) SEQUENCE DESCRIPTION: SEQ ID NO: 11:

```
Val Asn Glu Ala Ala Tyr Tyr
1               5
```

(2) INFORMATION FOR SEQ ID NO: 12:

(i) SEQUENCE CHARACTERISTICS:
        (A) LENGTH: 7 amino acids
        (B) TYPE: amino acid
        (D) TOPOLOGY: linear (v) FRAGMENT TYPE: internal (xi) SEQUENCE DESCRIPTION: SEQ ID NO: 12:

```
Val Xaa Glu Xaa Xaa Xaa Tyr
1               5
```

(2) INFORMATION FOR SEQ ID NO: 13:

(i) SEQUENCE CHARACTERISTICS:
        (A) LENGTH: 26 amino acids
        (B) TYPE: amino acid
        (D) TOPOLOGY: linear (iii) HYPOTHETICAL: NO (v) FRAGMENT TYPE: internal (xi) SEQUENCE DESCRIPTION: SEQ ID NO: 13:

```
Leu Glu Asn Ser Thr Glu Ile Gln Arg Thr Gly Leu Glu Val Lys Pro
1               5                   10                  15
Phe Ile Thr Asn Pro Arg Ala Val Lys Lys
                20                  25
```

(2) INFORMATION FOR SEQ ID NO: 14:

(i) SEQUENCE CHARACTERISTICS:
        (A) LENGTH: 37 amino acids
        (B) TYPE: amino acid
        (D) TOPOLOGY: linear (iii) HYPOTHETICAL: NO (v) FRAGMENT TYPE: internal (xi) SEQUENCE DESCRIPTION: SEQ ID NO: 14:

```
Lys Pro Leu Ile Pro Xaa Asp Pro Val Phe Leu Thr Leu Asp Gly Lys
1               5                   10                  15
Thr Ile Ser Leu Gly Gly Asp Gln Thr Xaa Tyr Pro Xaa Phe Xaa Asn
                20                  25                  30
Glu Ala Ala Tyr Tyr
        35
```

(2) INFORMATION FOR SEQ ID NO: 15:

(i) SEQUENCE CHARACTERISTICS:
        (A) LENGTH: 24 amino acids
        (B) TYPE: amino acid -continued

```
        (D) TOPOLOGY: linear (iii) HYPOTHETICAL: NO (v) FRAGMENT TYPE: internal (xi) SEQUENCE DESCRIPTION: SEQ ID NO: 15:

Xaa Lys Val Asp Tyr Pro Arg Asn Glu Ser Gly Glu Ile Ser Ala Ile
1               5                   10                  15

Ile His Pro Lys Leu Gln Asp Gln
            20

(2) INFORMATION FOR SEQ ID NO: 16:

(i) SEQUENCE CHARACTERISTICS:
          (A) LENGTH: 16 amino acids
          (B) TYPE: amino acid
          (D) TOPOLOGY: linear (iii) HYPOTHETICAL: NO (v) FRAGMENT TYPE: internal (xi) SEQUENCE DESCRIPTION: SEQ ID NO: 16:

Xaa Xaa Xaa Ala Leu Asp Phe Ile Xaa Asn Phe Xaa Glu Xaa Lys Glu
1               5                   10                  15

(2) INFORMATION FOR SEQ ID NO: 17:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ix) FEATURE:
          (A) NAME/KEY: modified_base
          (B) LOCATION: 6
          (D) OTHER INFORMATION: /mod_base= i (ix) FEATURE:
          (A) NAME/KEY: modified_base
          (B) LOCATION: 15
          (D) OTHER INFORMATION: /mod_base= i (ix) FEATURE:
          (A) NAME/KEY: modified_base
          (B) LOCATION: 16
          (D) OTHER INFORMATION: /mod_base= i (ix) FEATURE:
          (A) NAME/KEY: modified_base
          (B) LOCATION: 18
          (D) OTHER INFORMATION: /mod_base= i (xi) SEQUENCE DESCRIPTION: SEQ ID NO: 17:

AARGTNGAYT AYCCNNGNAA                                           20

(2) INFORMATION FOR SEQ ID NO: 18:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ix) FEATURE:
          (A) NAME/KEY: modified_base
          (B) LOCATION: 9
          (D) OTHER INFORMATION: /mod_base= i (ix) FEATURE:
          (A) NAME/KEY: modified_base
```

(B) LOCATION: 11
            (D) OTHER INFORMATION: /mod_base= i (ix) FEATURE:
            (A) NAME/KEY: modified_base
            (B) LOCATION: 15
            (D) OTHER INFORMATION: /mod_base= i (xi) SEQUENCE DESCRIPTION: SEQ ID NO: 18:

TGRTCYTGNA NYTTNGGRTG                                           20

(2) INFORMATION FOR SEQ ID NO: 19:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO: 19:

CCGTGTACCC AGTGTT                                               16

(2) INFORMATION FOR SEQ ID NO: 20:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 20:

CTTCTGAATT GCAGAAATCA                                           20

(2) INFORMATION FOR SEQ ID NO: 21:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 21:

GTAAGACACC GTGTAAGATG                                           20

(2) INFORMATION FOR SEQ ID NO: 22:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: 6
            (D) OTHER INFORMATION: /mod_base= i (ix) FEATURE:
            (A) NAME/KEY: modified_base
            (B) LOCATION: 9
            (D) OTHER INFORMATION: /mod_base= i (ix) FEATURE:
            (A) NAME/KEY: modified_base
            (B) LOCATION: 18
            (D) OTHER INFORMATION: /mod_base= i (ix) FEATURE:
            (A) NAME/KEY: modified_base
            (B) LOCATION: 21
            (D) OTHER INFORMATION: /mod_base= i -continued (xi) SEQUENCE DESCRIPTION: SEQ ID NO: 22:

GGRTANACNG TYTGRTCNCC NCC                                          23

(2) INFORMATION FOR SEQ ID NO: 23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 12
        (D) OTHER INFORMATION: /mod_base= i (xi) SEQUENCE DESCRIPTION: SEQ ID NO: 23:

CCNMGNGCNG TNAARAARTG                                              20

(2) INFORMATION FOR SEQ ID NO: 24:

(i) SEQUENCE CHARACTERISTICS:
        (A) LENGTH: 4 amino acids
        (B) TYPE: amino acid
        (D) TOPOLOGY: linear (iii) HYPOTHETICAL: NO (v) FRAGMENT TYPE: internal (xi) SEQUENCE DESCRIPTION: SEQ ID NO: 24:

Asp Cys Thr Val
1

(2) INFORMATION FOR SEQ ID NO: 25:

(i) SEQUENCE CHARACTERISTICS:
        (A) LENGTH: 7 amino acids
        (B) TYPE: amino acid
        (D) TOPOLOGY: linear (v) FRAGMENT TYPE: internal (ix) FEATURE:
        (A) NAME/KEY: Active-site
        (B) LOCATION: 1..7
        (D) OTHER INFORMATION: /note= "Consensus sequence of catalytic
            center in esterases"

(ix) FEATURE:
        (A) NAME/KEY: Region
        (B) LOCATION: 5
        (D) OTHER INFORMATION: /note= "Amino acid 5 is glycine or
            alanine"

(ix) FEATURE:
        (A) NAME/KEY: Region
        (B) LOCATION: 7
        (D) OTHER INFORMATION: /note= "Amino acid 7 is glutamic

```
                                    acid or aspartic acid"

(xi) SEQUENCE DESCRIPTION: SEQ ID NO: 25:

Gly Xaa Xaa His Xaa Xaa Xaa
1                5

(2) INFORMATION FOR SEQ ID NO: 26:

(i) SEQUENCE CHARACTERISTICS:
        (A) LENGTH: 4 amino acids
        (B) TYPE: amino acid
        (D) TOPOLOGY: linear (v) FRAGMENT TYPE: internal (ix) FEATURE:
        (A) NAME/KEY: Active-site
        (B) LOCATION: 1..4
        (D) OTHER INFORMATION: /note= "Consensus sequence of catalytic
            center in esterases"

(ix) FEATURE:
        (A) NAME/KEY: Region
        (B) LOCATION: 4
        (D) OTHER INFORMATION: /note= "Amino acid 4 is phenylalanine
            or valine"

(xi) SEQUENCE DESCRIPTION: SEQ ID NO: 26:

Asp Xaa Xaa Xaa
1

(2) INFORMATION FOR SEQ ID NO: 27:

(i) SEQUENCE CHARACTERISTICS:
        (A) LENGTH: 7 amino acids
        (B) TYPE: amino acid
        (D) TOPOLOGY: linear (v) FRAGMENT TYPE: internal (ix) FEATURE:
        (A) NAME/KEY: Active-site
        (B) LOCATION: 1..7
        (D) OTHER INFORMATION: /note= "Consensus sequence of catalytic
            center in esterases"

(xi) SEQUENCE DESCRIPTION: SEQ ID NO: 27:

Val Xaa Glu Xaa Xaa Xaa Tyr
1                5
```